United States Patent
Touchet et al.

(10) Patent No.: US 12,251,144 B2
(45) Date of Patent: Mar. 18, 2025

(54) BONE FIXATION SYSTEM

(71) Applicant: Trilliant Surgical LLC, Houston, TX (US)

(72) Inventors: Tyler Joseph Touchet, Cypress, TX (US); Christopher Radzicki, Cypress, TX (US); Daniel Jobe, Houston, TX (US)

(73) Assignee: Trilliant Surgical LLC, Houston, TX (US)

( * ) Notice: Subject to any disclaimer, the term of this patent is extended or adjusted under 35 U.S.C. 154(b) by 401 days.

(21) Appl. No.: 17/684,617

(22) Filed: Mar. 2, 2022

(65) Prior Publication Data

US 2022/0183731 A1    Jun. 16, 2022

Related U.S. Application Data

(63) Continuation of application No. PCT/US2020/052644, filed on Sep. 25, 2020.
(Continued)

(51) Int. Cl.
*A61B 17/80* (2006.01)
*A61B 17/17* (2006.01)
*A61B 17/86* (2006.01)

(52) U.S. Cl.
CPC ...... *A61B 17/8052* (2013.01); *A61B 17/8014* (2013.01); *A61B 17/8605* (2013.01);
(Continued)

(58) Field of Classification Search
CPC .......... A61B 2017/564; A61B 17/8052; A61B 17/8014; A61B 17/8605; A61B 17/8635; A61B 17/8047; A61B 17/1728; A61B 17/8625; A61B 17/866; A61B 17/80; A61B 17/8033; A61B 17/8057; A61B 17/8061; A61B 17/808; A61B 17/56; A61B 17/17;
(Continued)

(56) References Cited

U.S. PATENT DOCUMENTS 6,974,461 B1 * 12/2005 Wolter ................... A61B 17/80
606/283
8,105,367 B2    1/2012 Austin et al.
(Continued)

FOREIGN PATENT DOCUMENTS

CA    2752685 A1    8/2010
DE    4343117 C2    11/1999
(Continued)

OTHER PUBLICATIONS

International Search Report and Written Opinion, issued Jan. 12, 2021 in PCT/US2020/052644.

*Primary Examiner* — Marcela I. Shirsat
(74) *Attorney, Agent, or Firm* — Veros Legal Solutions, LLP

(57) ABSTRACT

An embodiment includes a bone fixation system comprising: a plate; and a tool; wherein: (a) the plate includes a hole to receive a bone anchor, (b) the hole includes a shelf, (c) the shelf includes a number of recesses; and (d) the hole is unthreaded and includes no resilient parts; wherein: (a) a distal end of the tool includes one or more lobes, (b) a number of lobes is no greater than the number of recesses, (c) each of the one or more lobes is configured to mate with one of the recesses. Other embodiments are described herein.

15 Claims, 15 Drawing Sheets

Related U.S. Application Data

(60) Provisional application No. 62/907,104, filed on Sep. 27, 2019.

(52) U.S. Cl.
CPC ...... *A61B 17/8635* (2013.01); *A61B 17/1728* (2013.01); *A61B 17/8033* (2013.01); *A61B 17/8047* (2013.01); *A61B 17/8057* (2013.01); *A61B 17/808* (2013.01)

(58) Field of Classification Search
CPC ............ A61B 17/1703; A61B 17/1707; A61B 17/1739
USPC ....... 606/101, 280, 281, 286, 291, 298–299, 606/300, 301, 86 R, 87, 96–98, 86 B, 606/902, 915
See application file for complete search history.

(56) References Cited

U.S. PATENT DOCUMENTS

| | | |
|---|---|---|
| 8,382,807 B2 | 2/2013 | Austin et al. |
| 8,544,472 B2 | 10/2013 | Gaskell |
| 8,636,808 B2 | 1/2014 | Olson |
| 8,888,824 B2 | 11/2014 | Austin et al. |
| 8,940,028 B2 | 1/2015 | Austin et al. |
| 8,992,581 B2 | 3/2015 | Austin et al. |
| 9,060,789 B2 | 6/2015 | Weinstein |
| 9,220,602 B2 | 12/2015 | Olson |
| 9,387,028 B2 | 7/2016 | Olson et al. |
| 9,554,811 B2 | 1/2017 | Weinstein |
| 9,795,424 B2 | 10/2017 | Austin et al. |
| 9,931,220 B2 | 4/2018 | Olson |
| 9,987,062 B2 | 6/2018 | Epperly |
| 10,080,598 B2 | 9/2018 | Austin et al. |
| 10,092,337 B2 | 10/2018 | Austin et al. |
| 10,149,708 B2 | 12/2018 | Kim et al. |
| 10,258,395 B2 | 4/2019 | Pak et al. |
| 10,292,741 B2 | 5/2019 | Austin et al. |
| 10,327,822 B2 | 6/2019 | Austin et al. |
| 10,687,873 B2 | 6/2020 | Langdale et al. |
| 10,736,680 B2 | 8/2020 | Austin et al. |
| 10,743,922 B1 | 8/2020 | Touchet et al. |
| 2004/0127896 A1* | 7/2004 | Lombardo ......... A61B 17/8042 606/296 |
| 2008/0114359 A1 | 5/2008 | Murner et al. |
| 2010/0106196 A1 | 4/2010 | Erickson et al. |
| 2011/0295325 A1 | 12/2011 | Wagner et al. |
| 2013/0012945 A1* | 1/2013 | Chreene ............. A61B 17/1728 606/80 |
| 2013/0123856 A1* | 5/2013 | Fritzinger ............. A61B 17/80 606/280 |
| 2014/0207194 A1 | 7/2014 | Wolter |
| 2016/0089191 A1 | 3/2016 | Pak et al. |
| 2019/0269445 A1 | 9/2019 | Singh et al. |
| 2019/0290338 A1 | 9/2019 | Bosshard et al. |
| 2020/0323570 A1 | 10/2020 | Austin et al. |
| 2020/0390483 A1 | 12/2020 | Oberli et al. |

FOREIGN PATENT DOCUMENTS

| | | |
|---|---|---|
| EP | 1649819 A1 | 4/2006 |
| EP | 3000423 A1 | 3/2016 |
| EP | 2398414 B1 | 6/2017 |
| EP | 3284426 A1 | 2/2018 |
| EP | 3533403 A1 | 9/2019 |
| EP | 3701894 A1 | 9/2020 |
| ES | 1227379 Y | 6/2019 |
| KR | 101722747 B1 | 4/2017 |
| WO | 2005018472 A1 | 3/2005 |
| WO | 2019180565 A1 | 9/2019 |
| WO | 2020178470 A1 | 9/2020 |
| WO | 2020250052 A1 | 12/2020 |
| WO | 2021061166 A1 | 4/2021 |
| WO | 2021062102 A1 | 4/2021 |

* cited by examiner

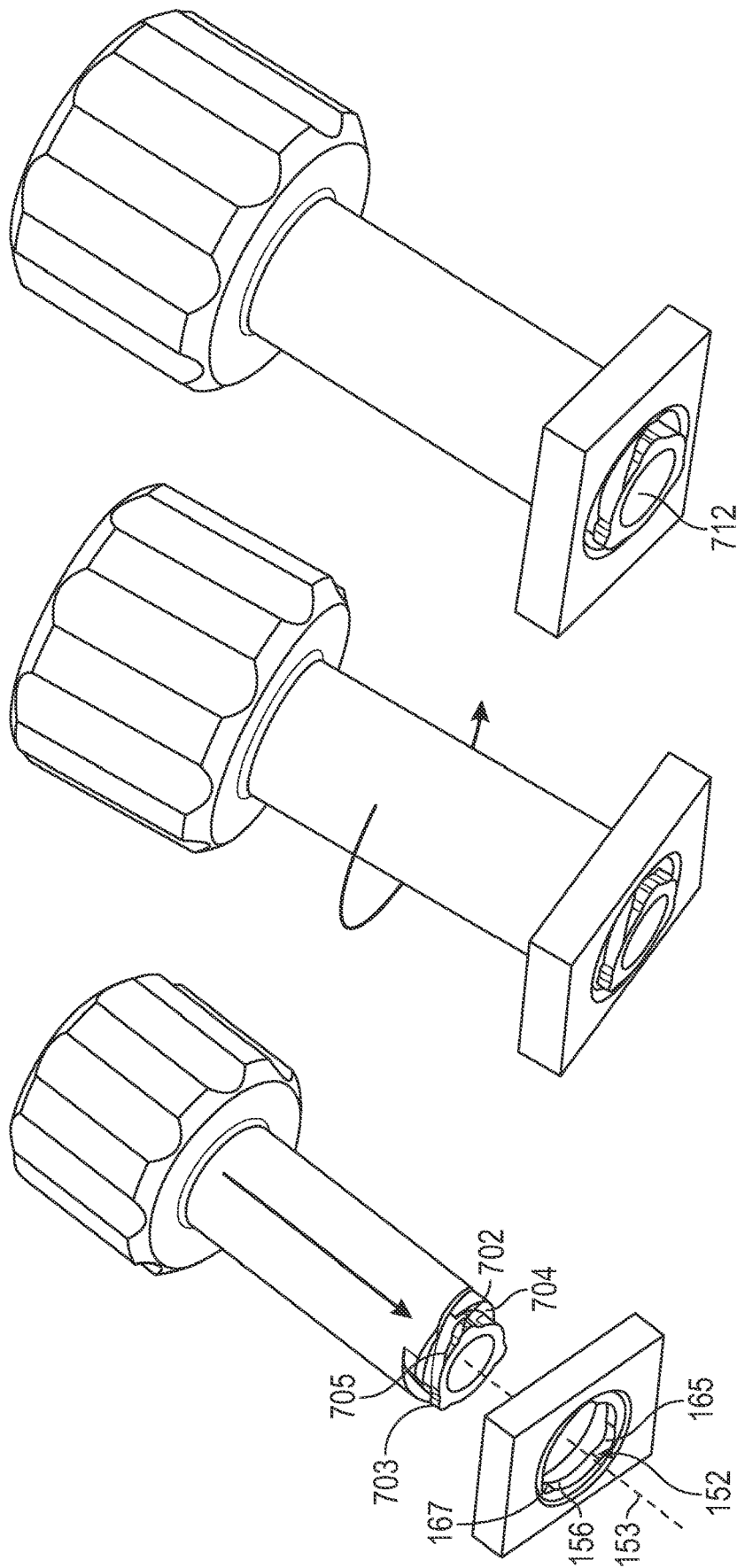

BONE FIXATION SYSTEM

CROSS REFERENCE TO RELATED APPLICATIONS

This application is a continuation of International Patent Application No. PCT/US2020/052644, filed on Sep. 25, 2020, which claims the benefit of U.S. Provisional Application No. 62/907,104, filed on Sep. 27, 2019, the contents of which are incorporated by reference herein in their entirety.

TECHNICAL FIELD

Embodiments of the invention are in the field of orthopedic applications.

BACKGROUND

It is common practice in orthopedics to drive bone screws into bone via holes in a fixation plate. This allows for the stabilization of osteotomies, fractures, bone fragments, and the like. Often a user may desire for a screw to lock to the plate to prevent the screw from backing out from the plate after insertion of the screw into bone. The desired angle at which a locked screw engages a hole in the plate may vary from normal to the central axis of the hole depending on patient anatomy or additional hardware.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIGS. 7A, 7B, 7C, 7D, 7E, 7F, 7G, 7H include perspective, side, and bottom views of a tool for plate handling in an embodiment.

DETAILED DESCRIPTION

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photo, may appear different while still incorporating the claimed structures of the illustrated embodiments. Moreover, the drawings may only show the structures useful to understand the illustrated embodiments. Additional structures known in the art may not have been included to maintain the clarity of the drawings. For example, not every portion of a device is necessarily shown. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner "Connected" may indicate elements are in direct physical or electrical contact with each other and "coupled" may indicate elements co-operate or interact with each other, but they may or may not be in direct physical or electrical contact. Phrases such as "comprising at least one of A and B" include situations with A, B, or A and B.

An embodiment includes a variable angle locking screw and plate system that does not require the plate include a threaded or tapered hole. Locking the screw to the plate allows for the biomechanical load to be transferred from the screw to the plate in a more efficient manner than would be the case with standard non-locking screw/plate systems. The load transfer may aid in the healing process as the reduction of, for example, the osteotomy or fracture is maintained.

Figure 2A:
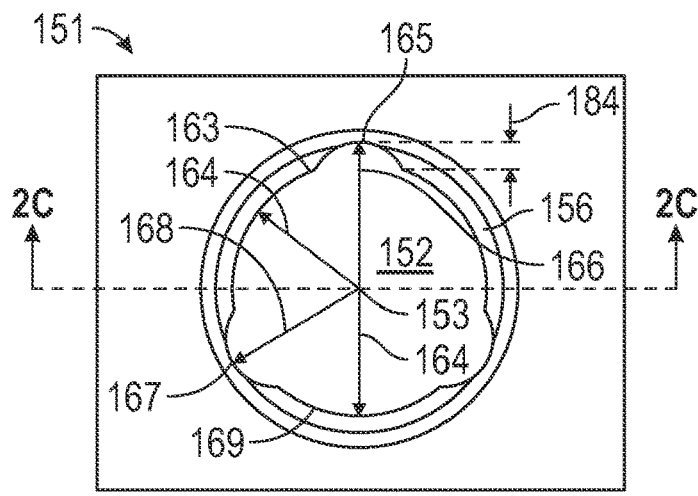
FIGS. 2A, 2B, 2C include a top view, a perspective view, and a cross-sectional view of a bone plate in an embodiment.

An embodiment includes a bone fixation system comprising a bone anchor 101 and a plate 151. While the plate in FIG. 2A shows a single aperture, this is for clarity and embodiments may include 1, 2, 3, 4, 5, 6 or more holes.

Figure 1:
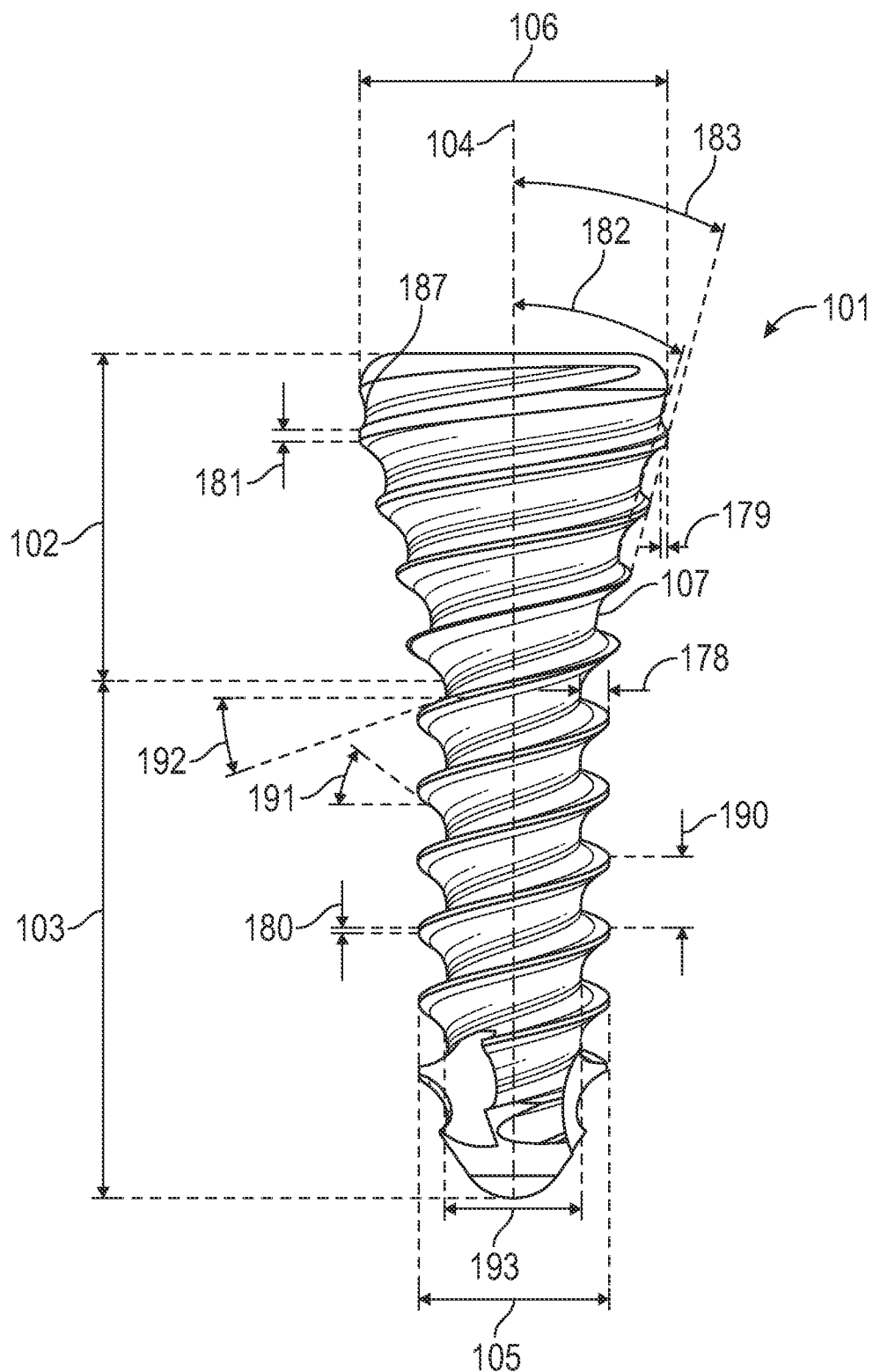
FIG. 1 includes a bone anchor in an embodiment.

The bone anchor includes a head 102, a body 103, and a long axis 104. The body has an outer diameter 105 that is orthogonal to the long axis and the head has an outer diameter 106 that is orthogonal to the long axis. While the body is not tapered in FIG. 1 other embodiment may have a tapered body wherein (a) the thread root 107 (where a thread meets the non-threaded portion of the body) may be tapered, (b) the thread crest (outermost edge of thread) may be tapered, (c) thread root and thread crest are both tapered at the same angle of incidence to the long axis, or (d) thread root and thread crest are tapered at different angles of incidence to the long axis. In FIG. 1 the outer diameter of the head diameter 106 is greater than the outer diameter of the body 105.

The plate includes an aperture 152 and the aperture includes a long axis 153 that traverses the aperture but does not intersect the plate. The aperture includes a first opening 154 and a second opening 155. The aperture includes a projection 156 and the projection projects inwardly from a wall 157 of the aperture and towards the long axis. The projection has a first surface 158 and a second surface 159. At least a portion of the first surface is coplanar with a first plane 160. The first plane 160 intersects the long axis at a first angle 161 which is 90 degrees. However, in other embodiments the first angle is between 85 degrees and 95 degrees, between 75 degrees and 105 degrees, or between 65 degrees and 115 degrees.

Projection 156 includes an inner wall 162 that couples the first surface of the projection to the second surface of the projection. The inner wall of the projection has a first portion 163 that is a first distance 164 from the long axis 153, the first distance being orthogonal to the long axis. The inner wall of the projection has a second portion 165 that is a second distance 166 from the long axis, the second distance being orthogonal to the long axis. The second distance is greater than the first distance due to portion 165 being in a void, recess, or relief formed along the wall 162. In an embodiment the inner wall of the projection has a third portion 167 that is a third distance 168 from the long axis, the third distance being orthogonal to the long axis. The third distance is greater than the first distance.

In an embodiment the third distance 168 is greater than the second distance 166 (not shown in FIG. 2A). Thus, reliefs may be formed at varying depths that are unequal to each other. The second distance is measured from a location of the second portion that is furthest from the long axis as compared to other locations of the second portion (i.e., the deepest portion of the relief) and the third distance is measured from a location of the third portion that is furthest from the long axis as compared to other locations of the third portion.

In an embodiment the inner wall of the projection defines an inner perimeter of the projection. The inner wall of the projection has a fourth portion 169 that is the first distance 164 from the long axis.

In an embodiment distance 166 is between 0.508 mm and 1.016 mm and is greater than distance 164 by a differential distance 184 and the differential distance is between 0.127 mm and 0.381 mm.

In an embodiment at least a portion of the second surface is coplanar with a second plane 170. The second plane intersects the long axis at a second angle 171 which is 90 degrees. However, in other embodiments the second angle is between 85 degrees and 95 degrees, between 75 degrees and 105 degrees, or between 65 degrees and 115 degrees.

Figure 2B:
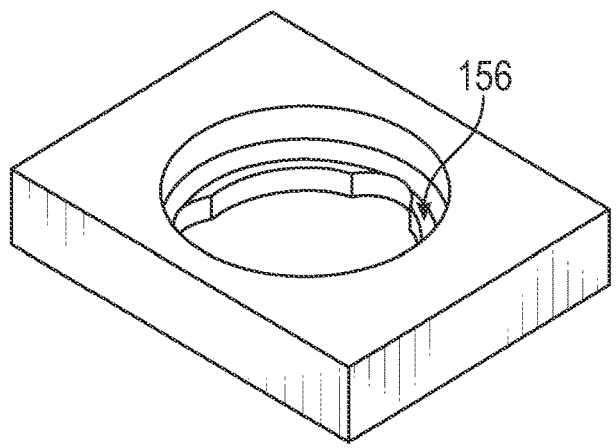
Figure 2C:
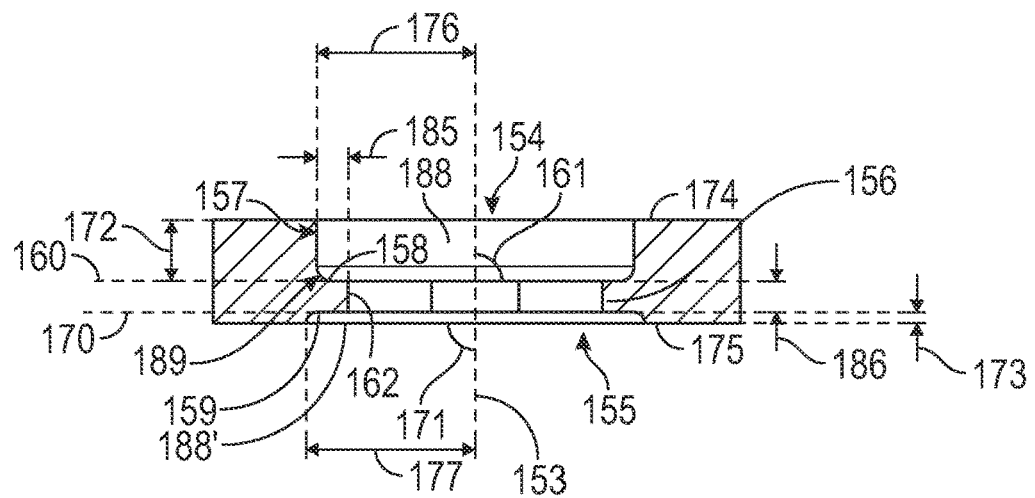

In FIG. 2C the first surface 158 is a first distance 172 from the first opening, the first distance being parallel to the long axis. The second surface is a second distance 173 from the second opening, the second distance being parallel to the long axis. The first distance is greater than the second distance. This may allow greater clearance for the plate to accept a bone anchor to thereby allow a greater angle of insertion of the anchor into the plate. However, in other embodiments these distances may be the same.

In an embodiment distance 173 is between 0.254 mm and 1.27 mm and distance 172 is between 0.254 mm and 5.588 mm. In an embodiment portion 163 of the projection projects inwardly from the wall 157 of the aperture and towards the long axis by distance 185 which is between 0.254 mm and 0.127 mm. In an embodiment thickness 186 is between 1.00 mm to 2.75 mm.

Dimensions as used herein are examples and various embodiment may or may not include such dimensions.

In an embodiment the plate 151 includes no threads between the first and second openings 154, 155. The first opening 154 directly interfaces a first outer surface 174 of the plate; the second opening 155 directly interfaces a second outer surface 175 of the plate; and the first outer surface 174 of the plate opposes the second outer surface 175 of the plate. By avoiding the use of threads, the locking angle can be increased without shearing the projection material off or creating burrs. Additionally, once a screw is locked in a threaded construct at an angle, the threads are damaged and relocking at different angles may be difficult. Avoiding threads allows for high angulation and repeated locks. Additionally, one is not limited by just one screw design or thread profile, unlike many other conventional locking constructs.

In an embodiment the first opening has a first maximum diameter (twice radius 176 in the example of FIG. 2C) that is orthogonal to the long axis and the second opening has a second maximum diameter (twice radius 177 in the example of FIG. 2C) that is orthogonal to the long axis. In an embodiment the second maximum diameter is greater than the first maximum diameter but in other embodiments the two diameters may be equal or the first diameter may be greater than the second diameter.

Figure 3C:
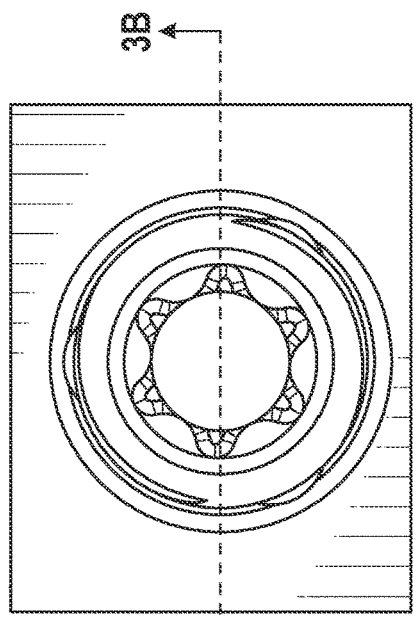
FIGS. 3A, 3B, 3C include a side view, a cross-sectional view, and a top view of a bone plate in an embodiment.
Figure 3B:
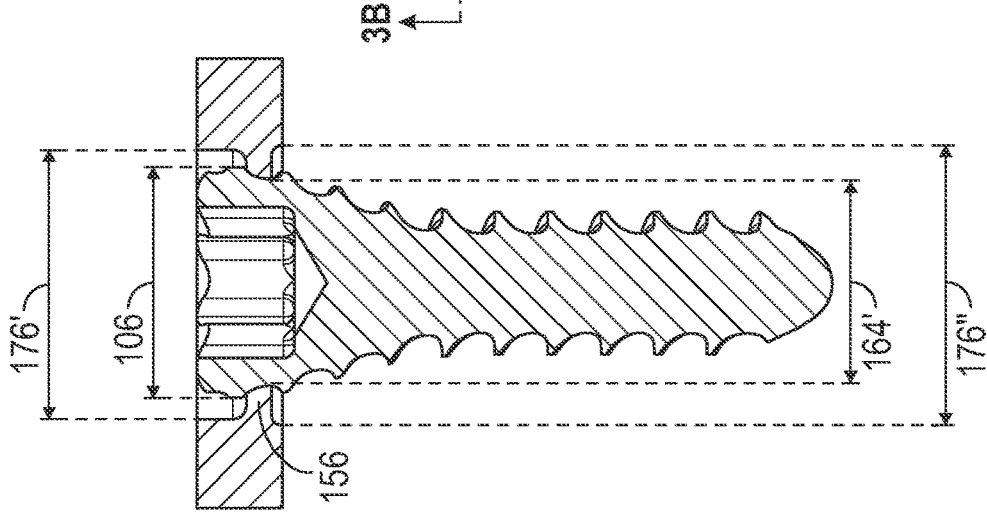
Figure 3A:
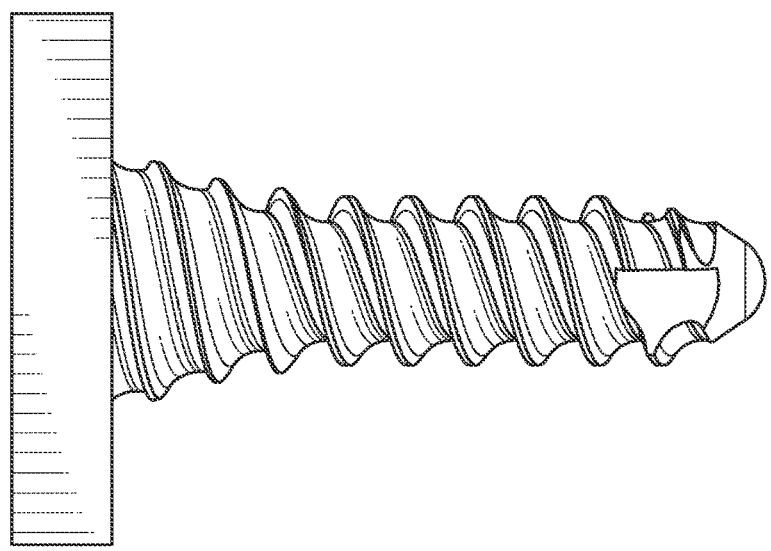

In FIG. 3B the head 102 of the bone anchor includes a maximum diameter 106. Plate opening 154 maximum diameter 176' is greater than the maximum diameter 106. Also, projection 156 forms a ring that circumnavigates an inner portion of the aperture. The ring has a minimum diameter 164' that is less than the maximum diameter 106. As used herein, a "maximum" diameter may accommodate situations where, for example, a surface is not circular. For example, opening 154 may be non-circular in some embodiments and therefore include more than one diameter such that the "maximum" diameter is the largest of the multiple diameters.

In an embodiment the maximum diameter 106 of the head of the bone anchor is between 5 percent and 10 percent larger than the minimum diameter 164' of the ring.

In FIG. 1 at least a portion of the head 102 of the bone anchor is included in a proximal-most fifth (20 percent) of the bone anchor and the portion includes threads. In other words, at least a portion of the bone anchor head is threaded. In FIG. 1 the body 103 of the bone anchor includes threads. The threads of the body of the bone anchor have a first thread height 178 and the threads of the portion of the head of the bone anchor have a second thread 179 that is less than the first thread height.

In FIG. 1 the threads of the body of the bone anchor have a first crest width 180 and the threads of the portion of the head of the bone anchor have a second crest width 181 that is greater than the first crest width. However, in other embodiments the widths 180, 181 are equal to each other and in still other embodiments width 181 that is less than width 180.

In FIG. 1 thread height 179 is between 0.0254 mm and 0.3048 mm and crest width 181 is between 0.0508 mm and 0.3048 mm.

Figure 4C:
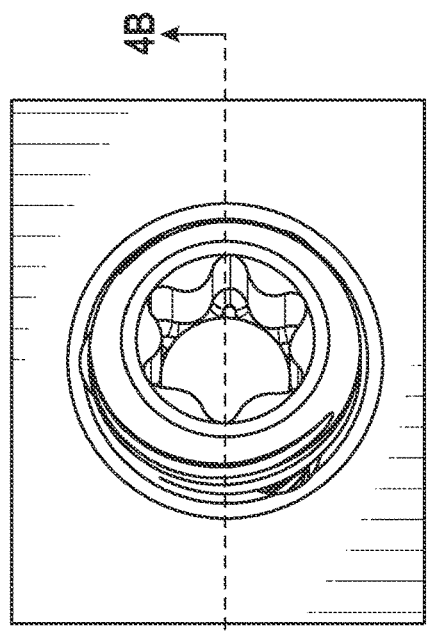
FIGS. 4A, 4B, 4C include a side view, a cross-sectional view, and a top view of a bone plate in an embodiment.
Figure 4B:
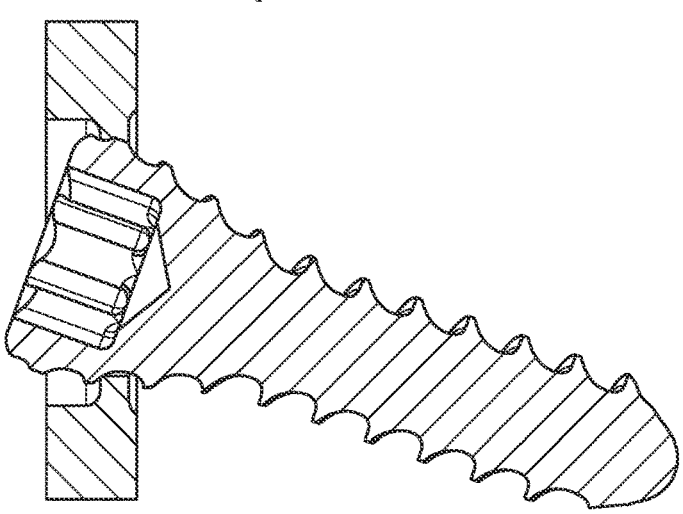
Figure 4A:
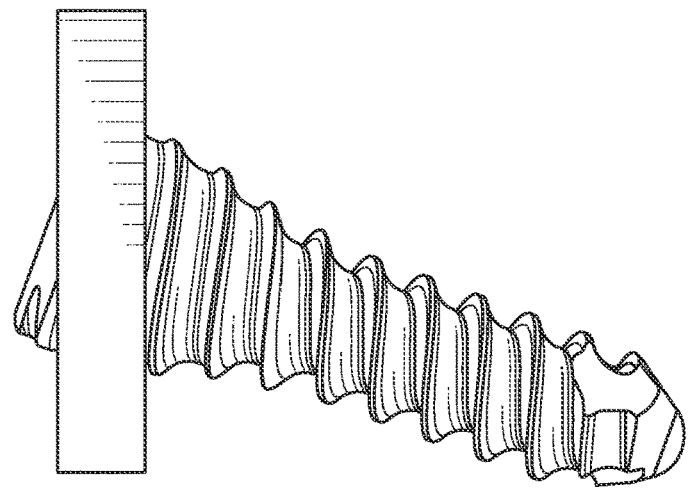

In FIGS. 1, 3C, and 4C the head of the bone anchor has a circular cross-section, the cross-section being orthogonal to the long axis of the bone anchor; and the outer diameter of the head is greater than the outer diameter of the body based on the bone anchor including a tapered portion. The tapered portion includes a thread root that tapers outwardly at an angle 182 between 10 degrees and 20 degrees. The threads of the portion of the head of the bone anchor include thread crests that taper outwardly at an angle 183 between 10 degrees and 20 degrees. However, in other embodiments the tapered portion includes a thread root that tapers outwardly at an angle 182 between 10 degrees and 25 degrees and the threads of the portion of the head of the bone anchor include thread crests that taper outwardly at an angle 183 between 10 degrees and 25 degrees.

An embodiment provides a variable angle locking construct for orthopedic applications by allowing for interference between the locking screw and the screw hole. In an embodiment the locking screw is a dual lead locking screw with a tapered diameter that (measured from one or more thread crests) extends 2.2 mm to 3.5 mm. However, in other embodiments the locking screw is a dual lead locking screw with a tapered diameter that (measured from one or more thread crests) extends 1.6 mm to 7.0 mm. In an embodiment the threaded portion extends throughout the length of the screw. The minor of the screw head is tapered by 12 degrees to 17 degrees and from 8 percent to 80 percent of the total screw length. The major of the screw head is tapered by 7 degrees to 15 degrees but not for the entirety of the head. The proximal portion of the screw head major is not tapered for 5 percent to 15 percent of the screw head. The screw has a minor diameter at the thread breakout 187 ranging from 6 percent smaller to 3 percent larger than diameter 164'. However, in another embodiment the screw has a minor diameter at the thread breakout 187 ranging from 10 percent smaller to 5 percent larger than diameter 164'.

In an embodiment the diameter of the locking threads on the anchor head range from 1 percent to 15 percent larger than diameter 164'. The difference in diameters provides interference with the projection 156 to cause deformation to the aperture at the relief cuts of portions 165, 167 (and any other relief cuts or portions in projection 156).

In an embodiment the anchor contains a diameter 106 that allows for limited interference with the top surface 174 under angulated locking up to 30 degrees from axis 104. However, in another embodiment the anchor contains a diameter 106 that allows for limited interference with the top surface 174 under angulated locking up to 50 degrees from axis 104.

In an embodiment space 188 is formed as a counterbore with a diameter 176' 15 percent to 35 percent larger than diameter 164'. The aperture formed by sidewall 162 is coaxial with the counterbore and allows for mating with the locking screw. Diameter 164' provides interference with the tapered head 102 and locking threads of the head. A radius 189 ranging from 0.0508 mm to 0.381 mm may be present at the bottom of the counterbore to aid in the reduction of stress or manufacturability.

The projection 156 includes a thickness 186 that 40 percent to 60 percent less than the lead of the screw 190 (where a lead is the axial advance of a helix or screw during one complete turn (360°) and wherein the lead for a screw thread is the axial travel for a single revolution).

The locking hole may have a plurality of relief cuts (see, e.g., portions 165, 167) that are radially oriented about the aperture. The presence of the cuts (or, more generally, voids) allows for deformation of the land to occur which aids in the interference fit with the screw.

In an embodiment anchor and plate are made of the same material. Such a material may include, for example, Ti-6Al-4V. However, other biocompatible materials may be used in other embodiments and the anchor and plate do not necessarily require the same material.

Embodiments are suitable for locking bone plates and anchors (such as screws) used for foot/ankle treatment. However, other embodiments are suitable for orthopedics or medicine (human or animal) in general including without limitation applications in foot and ankle, spinal, craniofacial, and/or veterinary arenas and the like.

Embodiments provide for a variable angled locking construct that does not use a tapered plate, threaded plate, or channeled plate.

The relief cuts or voids of the plate may include, 1, 2, 3, 4, 5 or more in alternative embodiments. An embodiment has an absence of the bottom side counterbore (e.g., void 188' is missing). Diameter 164' may range, for example, from 1.0 mm to 7.0 mm or more. Likewise, the anchors may vary in diameter 106 from 1.0 mm to 7.0 mm or more. In an embodiment the screw is not fully threaded and possesses a cap at the head of the screw that does not contain threads. In an embodiment the drive feature of the screw can be of any feature that allows for the transmission of torque from a mating member. In an embodiment the threads of the screw could be embodied in a left-handed thread configuration. In an embodiment the number of screw leads can vary from one to four. In an embodiment the screw head could be spherical in shape as opposed to conical in shape.

An embodiment includes a locking mechanism that locks using a mixture of the "cut-in", "point loading thread-in", and "screw head expansion" and mechanism without the use of a countersink, threaded hole, or tapered hole geometry. Compared to conventional technologies using a two-component system for locking, locking mechanisms addressed herein provide a higher degree of angulation without a compromise in the locking strength. Advantages over conventional systems include the ability to lock at angles exceeding 30 degrees in one direction, which results in a locking cone of 60 degrees. However, in other embodiments advantages over conventional systems include the ability to lock at angles exceeding 50 degrees in one direction, which results in a locking cone of 100 degrees. Additionally, an embodiment allows for multiple locking attempts at varying angles (without using additional components such as a bushing or locking cap). Instead, such an embodiment only requires a locking hole and screw of certain geometries to achieve the same result.

An embodiment includes a screw with two or more continuous threads. The screw includes a conical head and a cylindrical body that make up the overall length of the screw 201. Embodiments of a screw may vary in length from 4 mm to 170 mm. In an embodiment the length is between 8 mm to 50 mm.

In an embodiment the screw has a tapered conical head that extends to the cylindrical body of the screw. In the embodiment the screw is generally cylindrical between the tapered head and the tip of the screw.

In an embodiment the diameter of the screw head is a critical dimension. The diameter 106 of the screw head is imperative for interference that allows for the locking of the screw to the plate and which prevents the screw from translating through the hole without "biting" or locking. The diameter 106 of the screw head can vary from 2.4384 mm to 4.572 mm. In the embodiment the head diameter is equal or larger than diameter 164'. In an embodiment the diameter 106 is 7 percent larger than diameter 164'. However, in other embodiments the diameter 106 is 4, 5, 6, 8, 9, 10 percent larger or more than diameter 164'.

In an embodiment the thread height 178 (for the threads on the body) ranges from 0.254 mm to 0.762 mm. In an embodiment the height 178 is 0.381 mm. The thread height is identical between the two threads of the embodiment of FIG. 1 but in other embodiments they can be different with one thread having a larger height than the other.

In an embodiment a critical feature is that the thread height 181 at the head of the screw is different from the thread height 178 for the body of the screw. The thread height 181 is between 0.0254 mm and 0.3048 mm. In an embodiment the thread height 181 is 0.1778 mm. The height of the thread 181 in the tapered head 102 allows for ideal locking into the aperture formed by projection 156. If the thread height 181 is too high, the threads may deform and shear from the head of the screw creating an undesired burr of loose body. Conversely, if the thread height 181 is too low, the locking can be comprised by not contributing to a cut in projection 156.

In an embodiment a critical feature is that the minor head angle 182 (i.e., angle that the root of the thread follows). This feature is critical embodiment because it aids in the formation of the thread head geometry. In various embodiments the angle varies from 10 to 20 degrees and extends 80 to 100 percent of the tapered head 102 from the body of the screw 103. However, in other embodiments the angle varies from 10 to 25 degrees and extends 80 to 100 percent of the tapered head 102 from the body of the screw 103. The angle 182 allows for the threads on the head to bite and wedge into the projection 156.

In an embodiment a critical feature is that the major head angle 183 (i.e., angle that the thread crests follows). This feature is critical in an embodiment because it defines the geometry of the threads on the head. In various embodiments the angle may range from 10 to 20 degrees. However, in other embodiments the angle may range from 10 to 25 degrees. In an embodiment angle 183 is between 15 to 17 degrees. In an embodiment this angle is constant throughout the head of the screw. The angle allows for the threads on the head to bite and wedge into projection 156.

In an embodiment the leading flank angle 191 helps to define the thread geometry and is between 30 and 40 degrees (or between 20 and 50 degrees in other embodiments). In an embodiment angle 191 is 35 degrees. In an embodiment the trailing flank angle 192 helps to define the thread geometry and is between 2 and 8 degrees (or between 2 and 30 degrees in other embodiments). In an embodiment angle 192 is 3 degrees. In an embodiment the lead 190 of the screw (i.e., the pitch divided by each unique thread) is between 0.7366 mm and 1.524 mm. In an embodiment the lead is 0.9906 mm. In an embodiment the crest width 180 (or flats at the edge of the threads) on the body of the screw are between 0.0254 mm and 0.1524 mm.

In an embodiment a critical feature is that the crest width 181 on the head of the screw is/are between 0.0508 mm and 0.3048 mm, with a value being 0.2032 mm in an embodiment. This is critical because the crest needs to be small enough to produce enough stress and/or strain on the projection 156 but large enough so that it does not shear and create a loose body.

In an embodiment thread diameter 105 is the maximum diameter of the threads at the body of the screw. In an embodiment the diameters of all unique threads are equal (e.g., if there are two unique threads on the screw the threads are equal to each other). However, in an embodiment the diameters of all unique threads may be different. In an embodiment diameter 105 is about 2.6924 mm.

In an embodiment the shaft diameter 193 (defined by the diameter created by the root of thread for the body of the screw) is equal for all unique threads and may be about 1.8796 mm. However, in other embodiments diameter 193 may be different for different unique threads. In an embodiment the tip of the screw may be rounded or sharp for self-drilling applications. In an embodiment, root 107 of the thread is made up of two or more geometries such as radii (e.g., 0.2032 mm) and a 0.0254 mm flat.

Regarding the plate, in an embodiment a critical feature includes a use of an upper counterbore. As used herein, a counterbore is a cylindrical flat-bottomed hole that enlarges another coaxial hole. The use of the counterbore creates a flat land 158 that the locking screw can engage. The counterbore may have a depth 172 of 0.762 mm but may range in other embodiments from 0.254 mm to 1.27 mm. In alternative embodiments (e.g., FIG. 5B), the upper portion of the counterbore may have a countersink with total included angle greater than 90 degrees from the central axis 153. As used herein, a countersink includes a conical hole cut into a manufactured object. In embodiment, the counterbore radius 189 may or may not be present and allows for manufacturability of the land feature. Such a radius may be, for example, 0.254 mm.

In an embodiment aperture reliefs are a critical component. For example, in FIG. 2A there are three reliefs but in alternative embodiments there may be 1, 2, 4, 5 or more reliefs. The reliefs are oriented radially from the central axis 153 and are comprised of a diameter 166 ranging from 0.508 mm to 1.016 mm that protrudes into projection 156. The reliefs allow for deformation of the locking hole to occur without creating a loose body.

In an embodiment projection 156 (e.g., a land) is a projection of material that is radially oriented with an upper and lower surface that may be parallel to each other. In an embodiment there is no taper, angulation, or threaded relief to the land (e.g., there is a 90-degree angle between wall 162 and surface 158). The land may increase along the short axis of the locking hole (aperture formed by projection 156) if the underside of the locking plate is curved. The land is comprised of a thickness 186 and length 185.

In an embodiment the thickness 186 is critical to the function of the locking mechanism and is between 0.254 mm and 5.588 mm which allows for the thread of the locking head to cut into the projection without critically deforming the projection and allowing the screw to pull through the projection. The land thickness 186 is consistent around the circumference of the aperture in an embodiment. In an embodiment thickness 186 varies. Such an embodiment may include, for example, steps to vary the thickness.

In an embodiment 176' is larger than diameter 164' by 1.0668 mm. The smaller the counterbore diameter is the less angulation the screw can be locked in because the screw will contact the top surface 174. In alternative embodiments the presence of a countersink at the top of the counterbore circumvents this consideration.

In an embodiment a critical feature is the depth 184 of the reliefs, which may or may not be equal for each of the reliefs. Typically, the reliefs will have a depth 184 into the projection 156 from 0.127 mm to 0.381 mm. In an embodiment depth 184 is 0.3048 mm. If the depth of the relief is too shallow, the locking will be compromised. Similarly, if the depth is too deep the land may subject to a critical force and the land will deform too much and shear from the locking plate.

In an embodiment diameter 164' is a critical feature. The diameter is less than the head diameter 106 by 7 percent but may range from 2 to 15 percent less. The diameter is critical to the design and allows for the optimal amount of interference that allows the screw to bite/wedge into the locking hole (hole defined by projection 156) to create a solid one-piece construct. In an embodiment, the aperture has a diameter of 4.0767 mm.

Figure 5A:
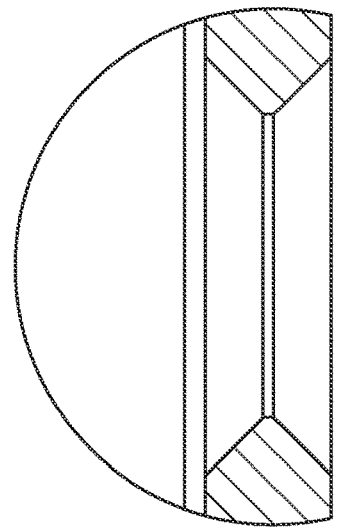
FIGS. 5A, 5B, 5C include cross-sectional views of differing embodiments of a bone plate.
Figure 5B:
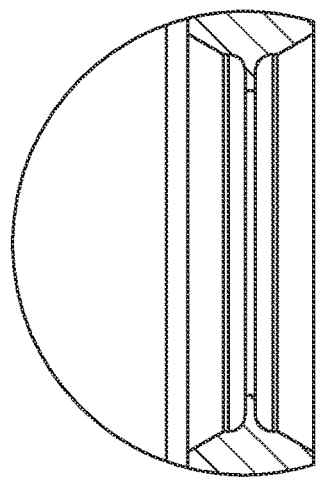
Figure 5C:
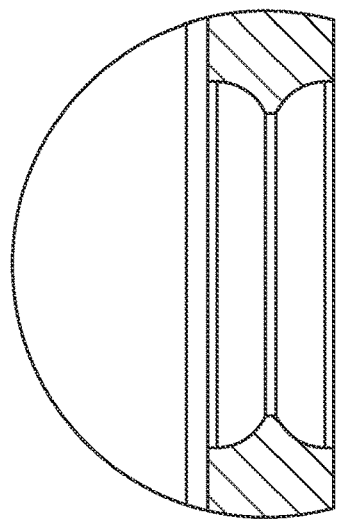

In an embodiment the upper counterbore depth has a sidewall 157 parallel with axis 153. However, a counterbore can be combined with other features such as a countersink (e.g., FIG. 5B). FIGS. 5A and 5C illustrate other alternative designs. In an embodiment the upper counterbore depth 172 is 0.889 mm.

In an embodiment a lower counterbore is present, but such a feature is optional. An embodiment includes a land with two parallel planes 160, 170. If a lower counterbore absent, the underside 175 may have a radius of curvature that is not parallel to the top surface 174 of the land. The presence of a lower counterbore or void aids in providing clearance of the locking screw at high angles. In an embodiment, the lower counter bore has a diameter 176" of 5.461 mm and a depth 173 of 0.127 mm.

A critical feature in some embodiments is the distance 185 of the projection of the locking hole land from the counterbore wall 157. This value may vary from 0.254 mm to 0.762 mm in various embodiments. The projection is critical to the locking mechanism because if the projection is too small, the angle that the screw and the ability to lock will be compromised. Additionally, if the projection is too long, the locking screw may translate through the locking hole.

In an embodiment, the angle of the upper counterbore wall 157 from the central axis 153 may be 0 degrees (parallel) but may range from 0 to 80 degrees in other embodiments. Further, the angle of the lower counterbore sidewall from axis 153 may be 0 degrees but may range from 0 to 80 degrees.

Various other embodiments are now addressed.

During surgical procedures, it is often desired for a screw to lock into a plate to prevent the screw from backing out after insertion. Additionally, utilizing a locking construct allows for the biomechanical load to be transferred from the screws to the plate in a more efficient manner than with standard screws. The transfer for the load can aid in the healing process as the reduction of the osteotomy or fracture is maintained.

Additionally, plates that allow for dynamic compression via an eccentric hole provide additional compressive force during the healing process. Conventionally, these holes do not allow for the anchor to lock into the plate which can lead to the screw backing out. However, embodiments (e.g., FIG. 6A) addressed lock anchors to the plate Furthermore, embodiments provide instrumentation (e.g., FIG. 7A) that interfaces with plates described herein such that the user can manipulate the spatial orientation or use the instrument as a guide in the preparation of voids (e.g., pilot holes in bone) to accept anchors. By having a device that interfaces with the locking hole of various plates described herein, users can move the plate in space as well as use the device to guide subsequent instrumentation, such as guiding a drill bit to the proper location.

FIGS. 6A-6M address a bone fixation system comprising plate 600 configured to mate with bone anchor 601. The plate includes first and second plate surfaces 602, 603 that oppose one another, first and second outer sidewalls 604, 605 that oppose one another and which do not include either of the first or second plate surfaces, and an aperture 606 that extends from the first plate surface to the second plate surface. The aperture includes a long axis 607 that traverses the aperture but does not intersect the plate. First and second inner sidewalls 608, 609 oppose one another. The first inner sidewall includes a first surface 610, and the first surface: (a) slopes away from the first plate surface and towards the second plate surface, (b) slopes away from the first outer sidewall and towards the second outer sidewall, and (d) is planar. Such a surface may include a portion of a wall or edge (and not necessarily the entire wall or edge). The first inner sidewall includes a second surface 611, and the second surface: (a) slopes away from the first plate surface and towards the second plate surface, (b) slopes away from the first outer sidewall and towards the second outer sidewall, and (d) is not co-planar with the first surface. The second surface may or may not be planar and may have portions that are planar and portions that are non-planar (e.g., curved).

Figure 6A:
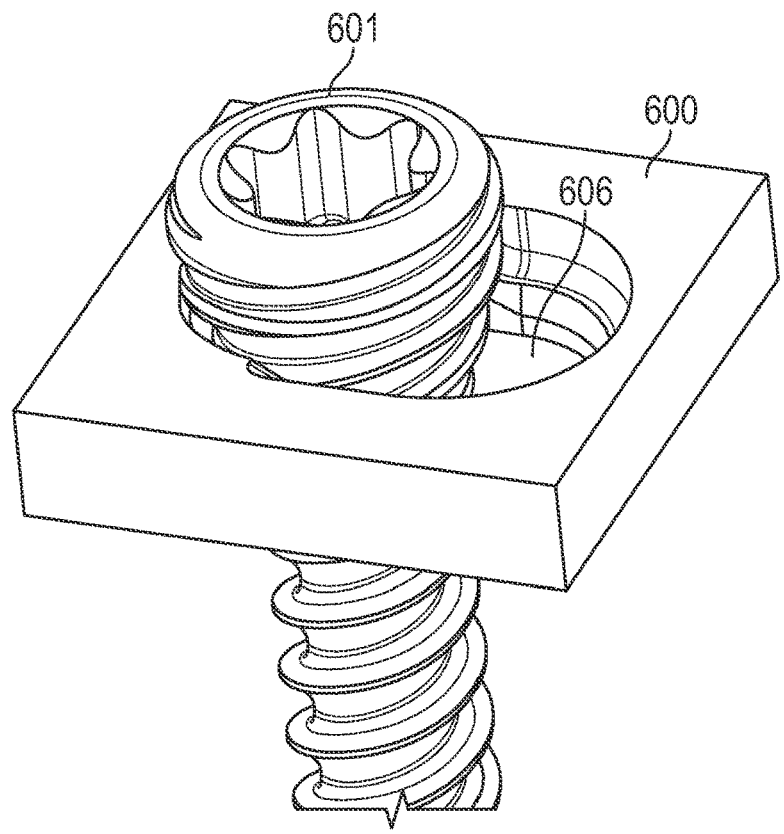
FIGS. 6A, 6B, 6C, 6D, 6E, 6F, 6G, 6H, 6I, 6J, 6K, 6L, 6M include perspective, top, and cross-sectional views of a compression plate in an embodiment. Such plates may include features of other embodiments described herein. For example, a plate of FIG. 6A may include the projection with reliefs shown in FIGS. 2A, 2B, 2C. A plate of FIG. 6A may be used with anchors such as the anchor of FIG. 1. A single bone plate may include apertures that include the apertures of FIG. 2A and FIG. 6A as well as other types of apertures.
Figure 6B:
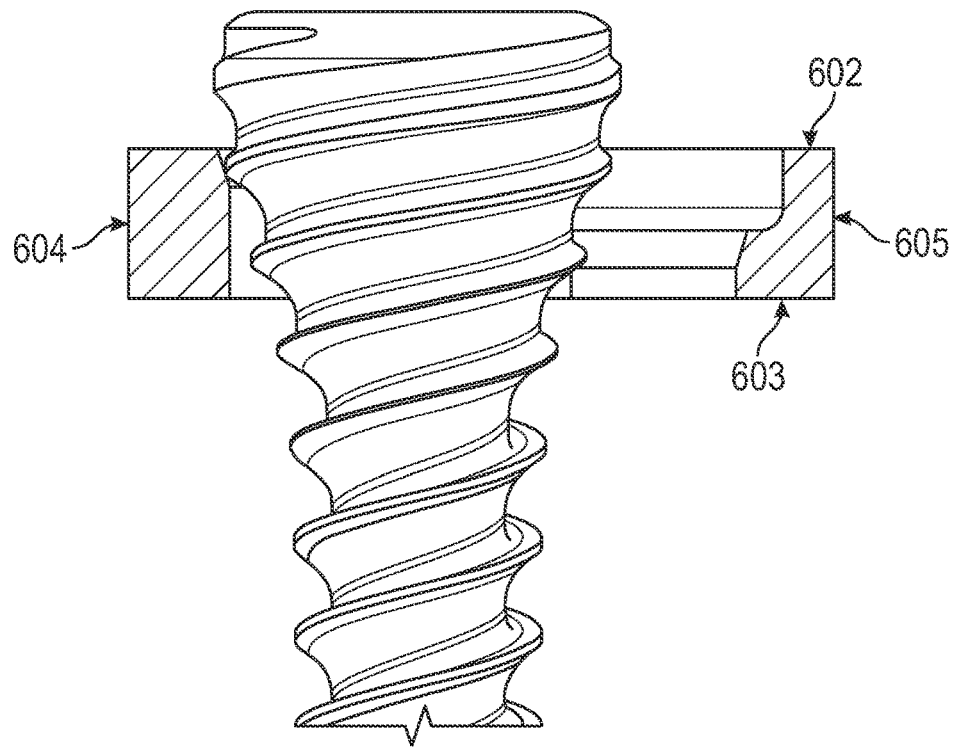
Figure 6C:
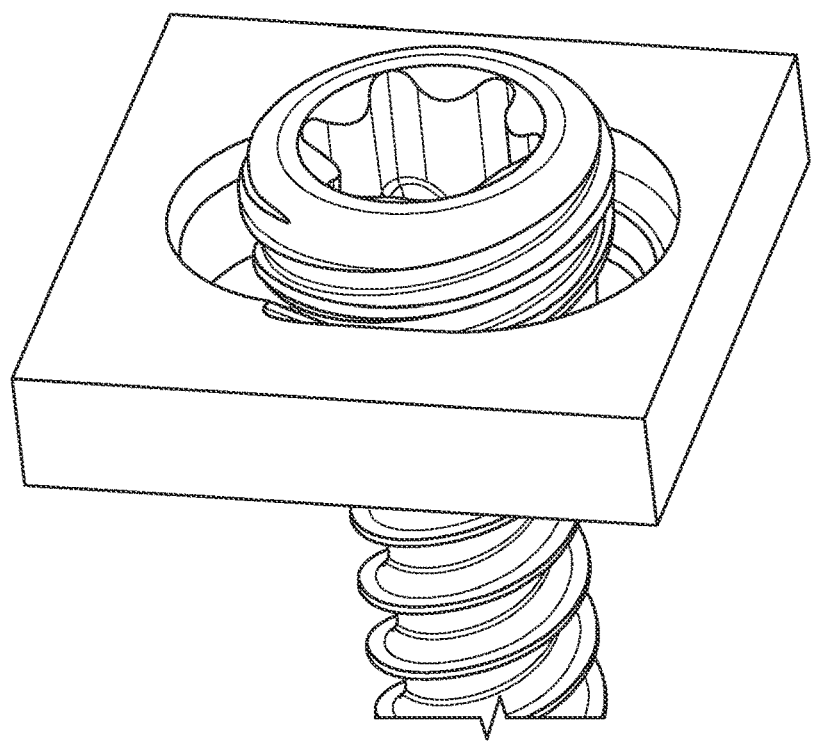
Figure 6D:
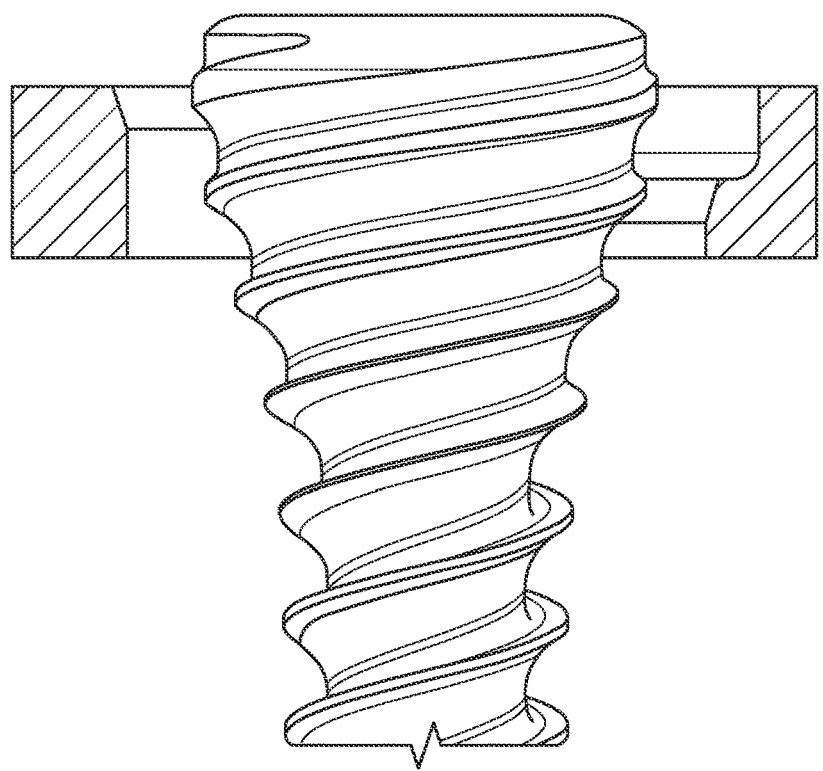
Figure 6E:
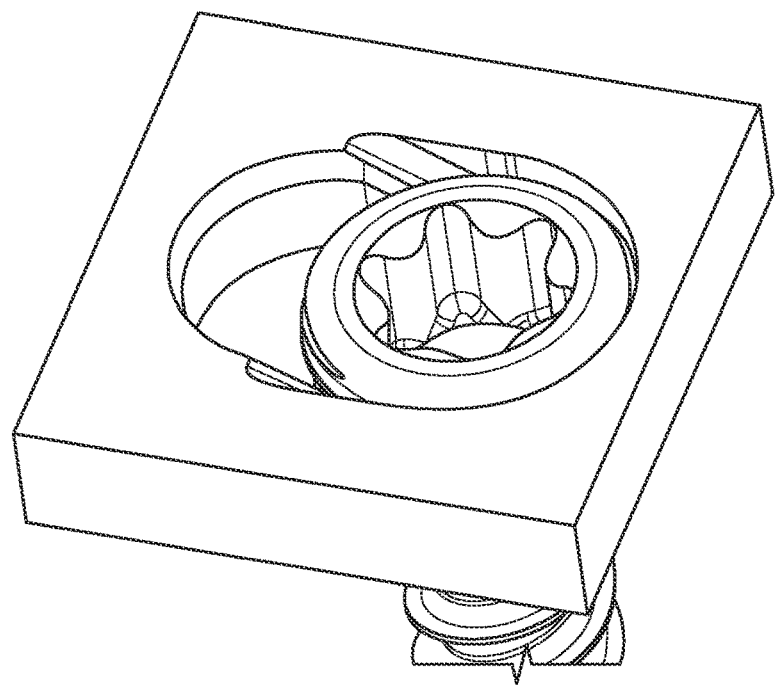
Figure 6F:
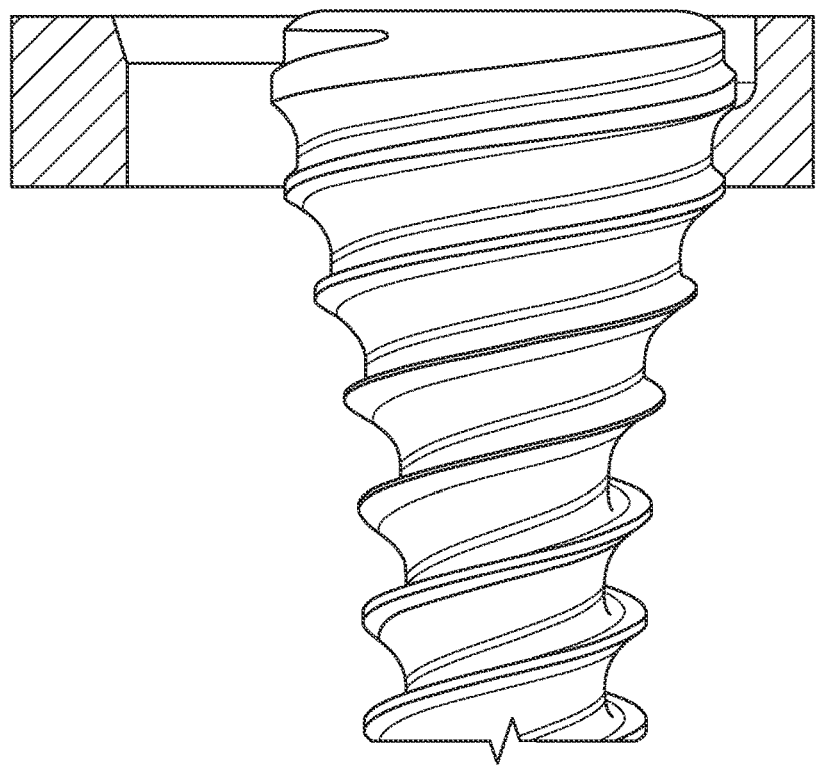

The embodiment of FIGS. 6A-6M is a variable angle compression locking construct. For instance, anchor 601 may lock to the plate in a polyaxial fashion. In other words, the anchor may lock to the plate at multiple angles. This is due in part to the lack of any threads in plate 600. Further, the compression occurs because as the anchor is turned the anchor engages first surface 610. As a result, the anchor travels down into the plate (slides horizontally and downwards) thereby pulling bones toward one another. For example, FIG. 6A shows only a portion of a plate. In a clinical setting plate 600 may include another aperture on an opposing side of a bone fracture. If the opposing side already has an anchor driven through the "another aperture", then causing anchor 601 to slide and traverse the eccentric hole 606 will cause the bone fractures to compress against one another.

Various materials, such as Ti-6Al-4V, may be used for both the anchor and the holes (e.g., holes of FIGS. 2A and/or 6A). However, other materials are acceptable as well such as biocompatible, non-corrosive materials including stainless steel or polymers (e.g., Polyether ether ketone (PEEK)). Metals may include martensitic or precipitation hardened metals. Embodiments addressed herein may be used for locking bone plates and screws for the foot/ankle. However, other embodiments are envisioned for any number of orthopedic or medical applications The embodiment of FIG. 6A allows for locking between the screw and aperture without the need for tapered, threaded, or channeled features. The eccentric hole of FIG. 6A allows for an interfacing anchor to be inserted and locked into place without the use of threads or a third component. The eccentric hole allows for increased compression of non-locking anchors, axial locking of locking anchors, and sustained dynamic compression because of the dual ramp design and distal projection. The eccentric hole allows for dynamic compression to be locked while having at least two mechanisms (two ramps per side of plate) to ensure the anchor translates down and across the plate.

In an embodiment first surface 610 is chamfered and second surface 611 is not chamfered. As used herein, a chamfer is a transitional edge between two faces of an object. Sometimes defined as a form of bevel, it is may be created at a 45° angle between two adjoining right-angled faces (but is not limited to such an angle) Chamfers are frequently used in machining, carpentry, furniture, concrete formwork, mirrors, printed circuit boards, and the like. The two surfaces the chamfer joins do not necessarily have to be orthogonal to each other.

Plate 600 includes a counterbore and the counterbore includes the second surface 611. Above a counterbore was addressed as being a cylindrical flat-bottomed hole (or having a portion of bottom be flat) that enlarges another coaxial hole. In the case of FIG. 6A, the cylindrical hole may be conjoined with another form to ultimately create the eccentric hole 606. Thus, the plate may include a hole and only a portion of that hole may include a counterbore or countersink.

First surface 610 may include first and second sloped edges 612, 613 that oppose one another. The second sloped edge is between the first sloped edge and the second plate surface. The first sloped edge is a first distance 614 from the long axis (with distance 614 measured orthogonal to the long axis 607). The second sloped edge is a second distance 615 from the long axis (with distance 615 measured orthogonal to the long axis 607). The second distance is smaller than the first distance. The first and second distances are in a plane 622 that is parallel to the long axis and which intersects the long axis. Such an arrangement provides advantages over conventional compression eccentric holes in that the use of dual ramps (surfaces 610, 611) ease translation of the anchor across the eccentric hole and promote a more full or longer translation. And as the length of horizontal anchor translation increases, so does the amount of compression and healing effects that correspond to compression.

In an embodiment, the second surface has a curved portion 660. The curved portion may be a radius between a flat portion 661 of surface 611 and a sidewall portion 662. In an embodiment, the second surface directly interfaces the first plate surface 602 at location 663 but not the second plate surface 603.

The second inner sidewall includes an additional first surface 610', and the additional first surface: (a) slopes away from the first plate surface and towards the second plate surface, (b) slopes away from the first outer sidewall and towards the second outer sidewall, and (d) is planar. The second inner sidewall includes an additional second surface 611', and the additional second surface: (a) slopes away from the first plate surface and towards the second plate surface, (b) slopes away from the first outer sidewall and towards the second outer sidewall, and (d) is not co-planar with the additional first surface. The additional first surface includes additional first and second sloped edges 612', 613' that oppose one another and the additional second sloped edge is between the additional first sloped edge and the second plate surface. The additional first sloped edge is an additional first distance 614' from the long axis and is measured orthogonal to the long axis; the additional second sloped edge is an additional second distance 615' from the long axis and is measured orthogonal to the long axis. The additional second distance is smaller than the additional first distance. The additional first and second distances are in the plane.

An additional plane 623 intersects the long axis 607 and is parallel to the long axis. The additional plane intersects the first and second outer walls 604, 605. The first sloped edge is the first distance 614 from the additional plane along a majority of an entire length of the first sloped edge. In other words, in an embodiment there is no tapering towards the middle of the hole along a length such as a majority of length 652. Similarly, the additional first sloped edge is the additional first distance 614' from the additional plane along a majority of an entire length of the additional first sloped edge. The first sloped edge 612 may be entirely linear along a majority of length 652 and will not taper towards the additional first sloped edge 612'. The second sloped edge may be entirely linear and not tapered towards the additional second sloped edge along a majority of length 652. As a result, a longer translation length of the anchor across the eccentric hole is possible.

Figure 6G:
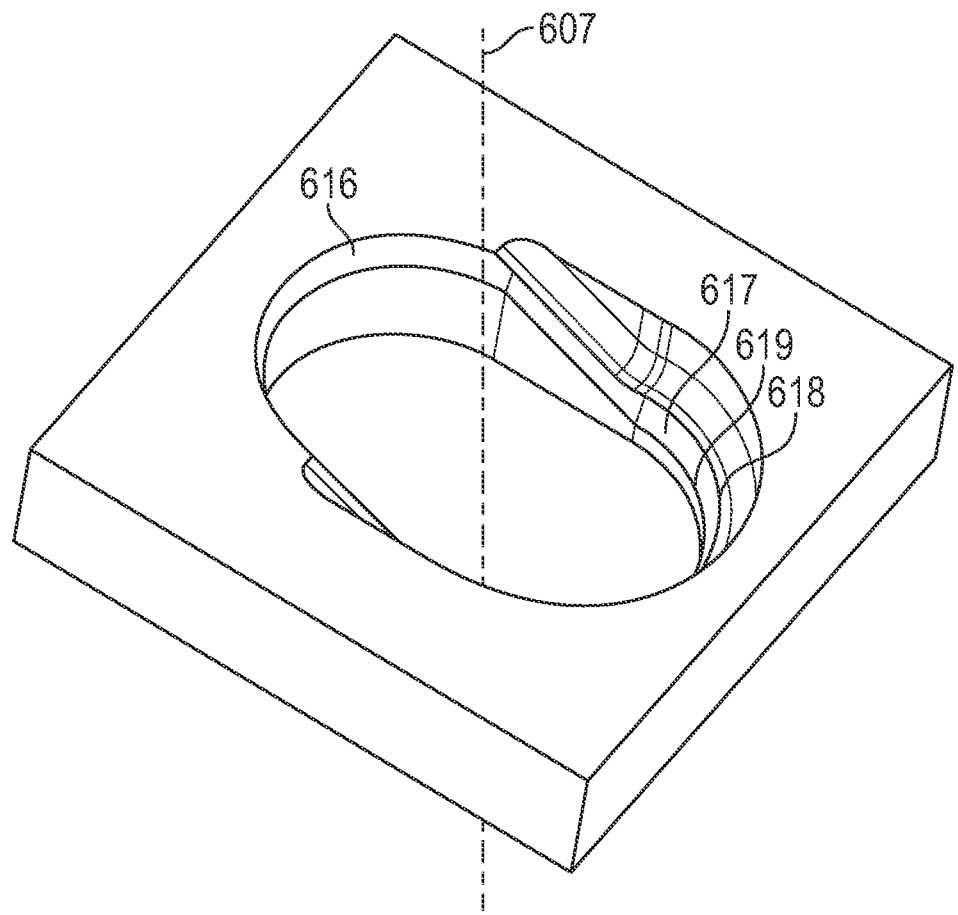
Figure 6H:
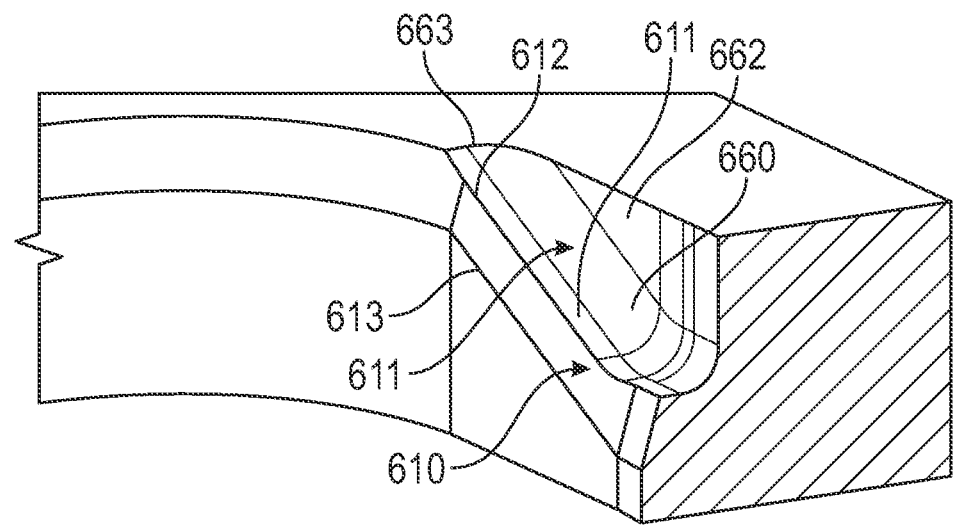
Figure 6I:
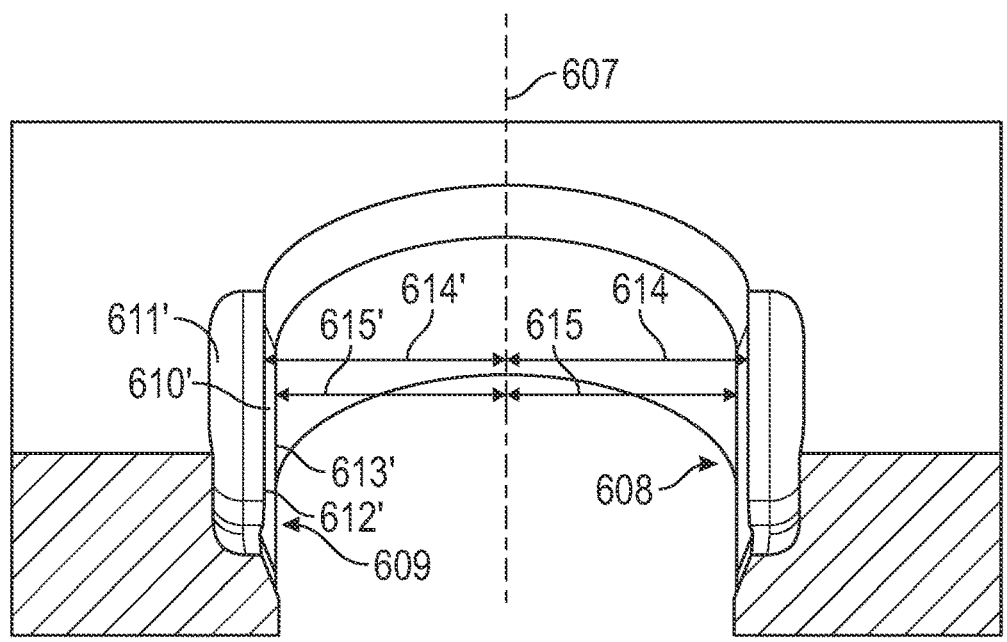
Figure 6J:
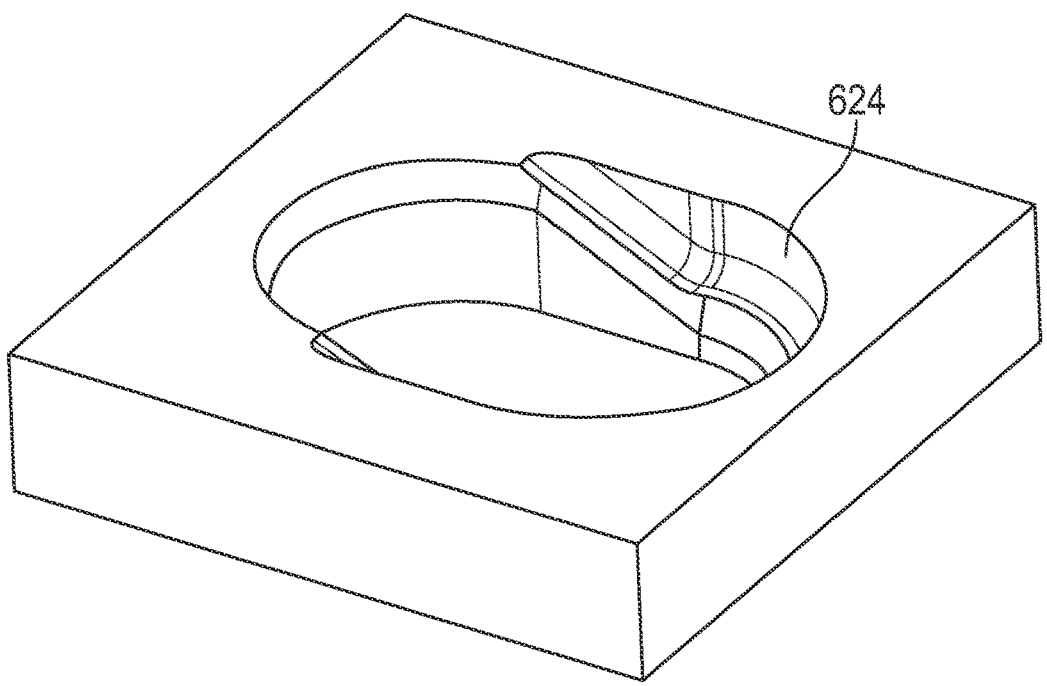
Figure 7A:
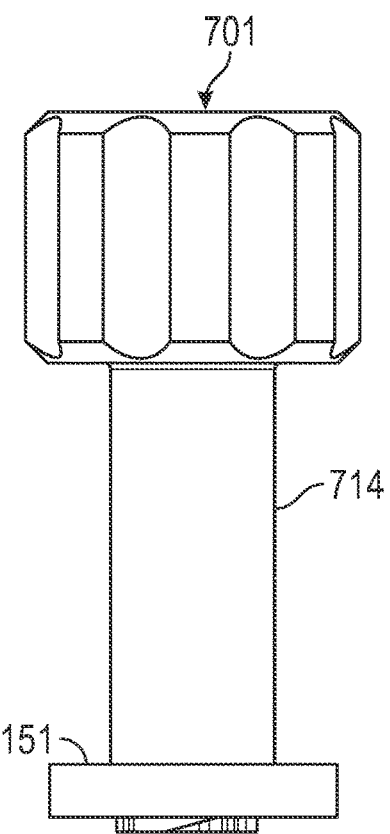
Figure 7E:
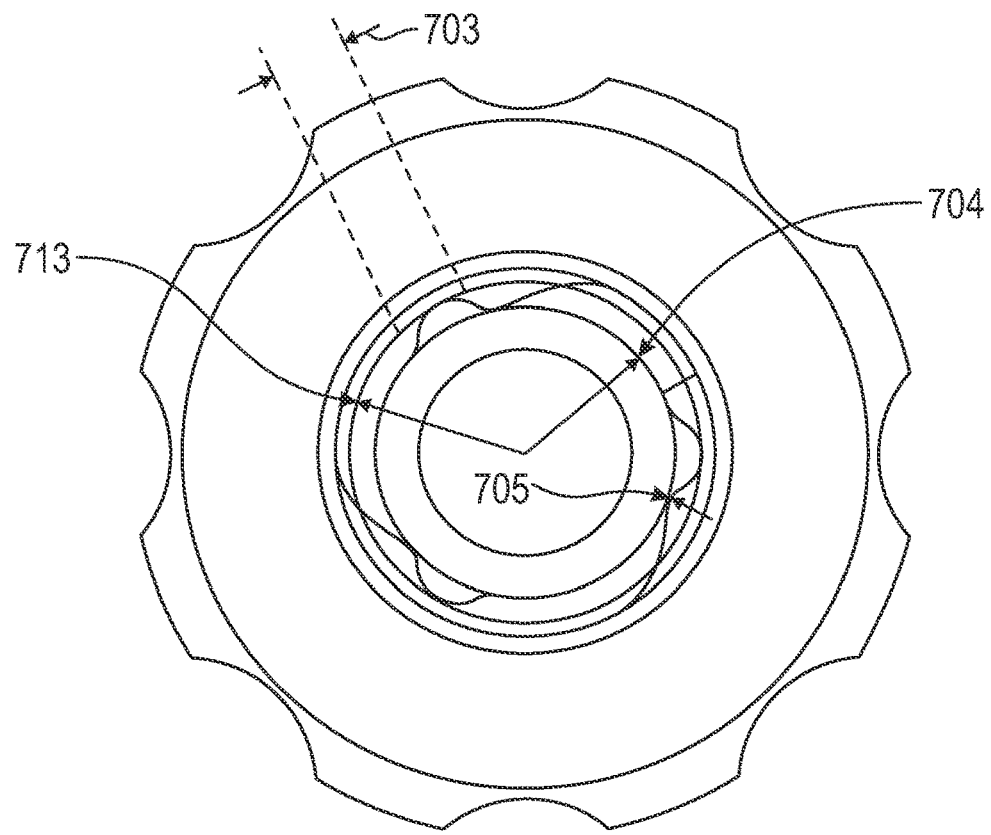
Figure 7F:
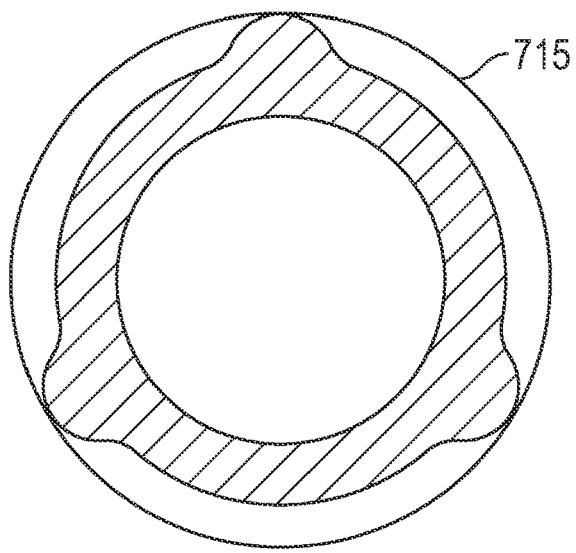
Figure 7G:
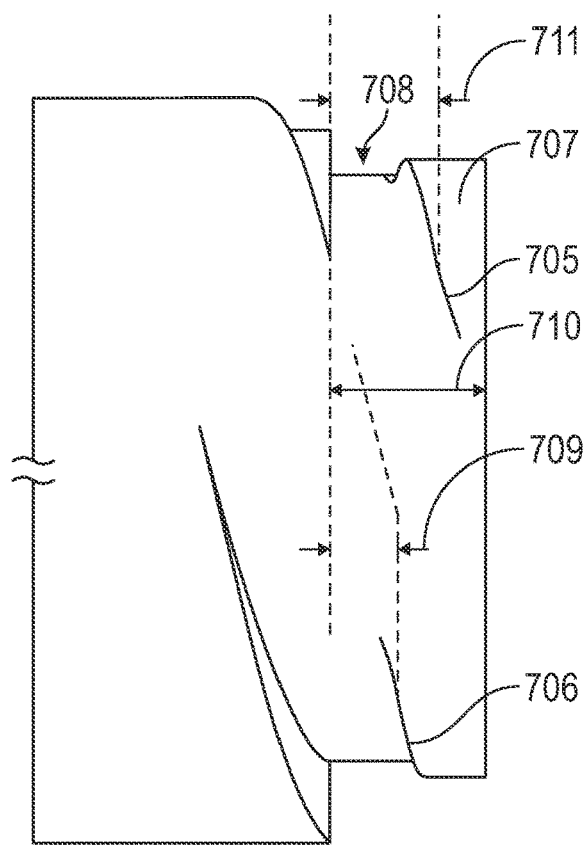

In FIG. 6G the plate comprises first and second curved surfaces 616, 617. The first curved surface couples the first surface 610 to the additional first surface 610' and the second curved surface couples the first surface 610 to the additional first surface 610'. The first curved surface is a third distance from the first plate surface. In the case of FIG. 6G, the third distance is 0 mm but other embodiments are not limited in this way. In FIG. 6G, the second curved surface is a fourth distance from the first plate surface and the third distance is less than the fourth distance. The third and fourth distances are in the additional plane.

In FIG. 6G the second curved surface includes first and second curved edges 618, 619 that oppose one another. The second curved edge is between the first curved edge and the second plate surface. The first curved edge is a fifth distance 620 from the long axis and is measured orthogonal to the long axis. The second curved edge is a sixth distance 621 from the long axis and is measured orthogonal to the long axis. The sixth distance is smaller than the fifth distance and the fifth and sixth distances are in the additional plane. In FIG. 6G, surface 617 is chamfered to result in the above arrangement.

Figure 6K:
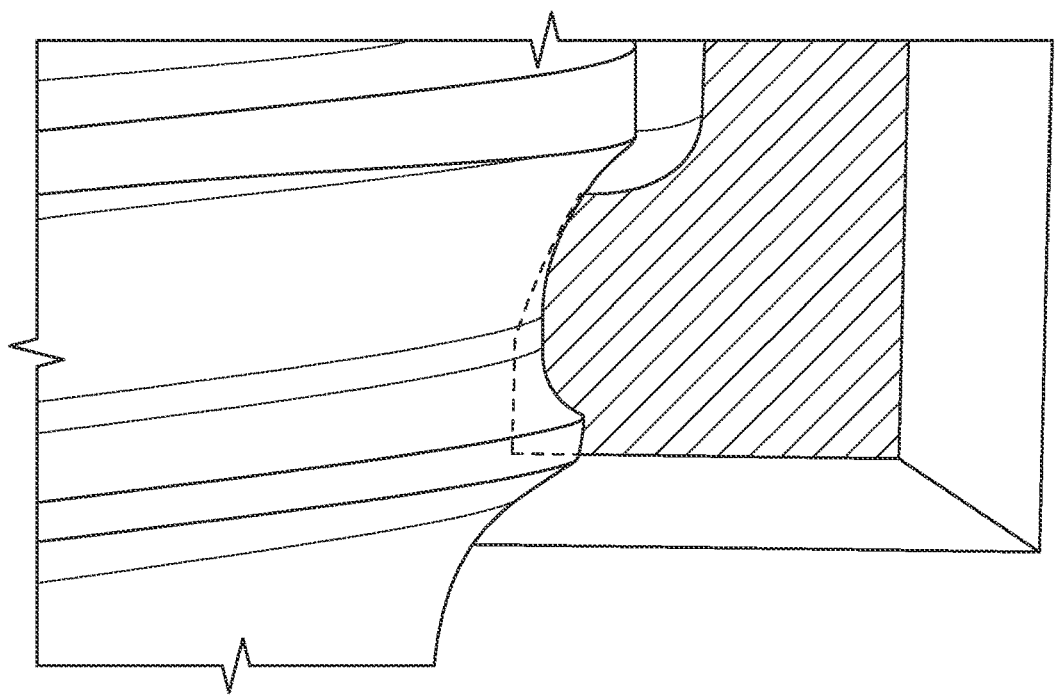
Figure 6L:
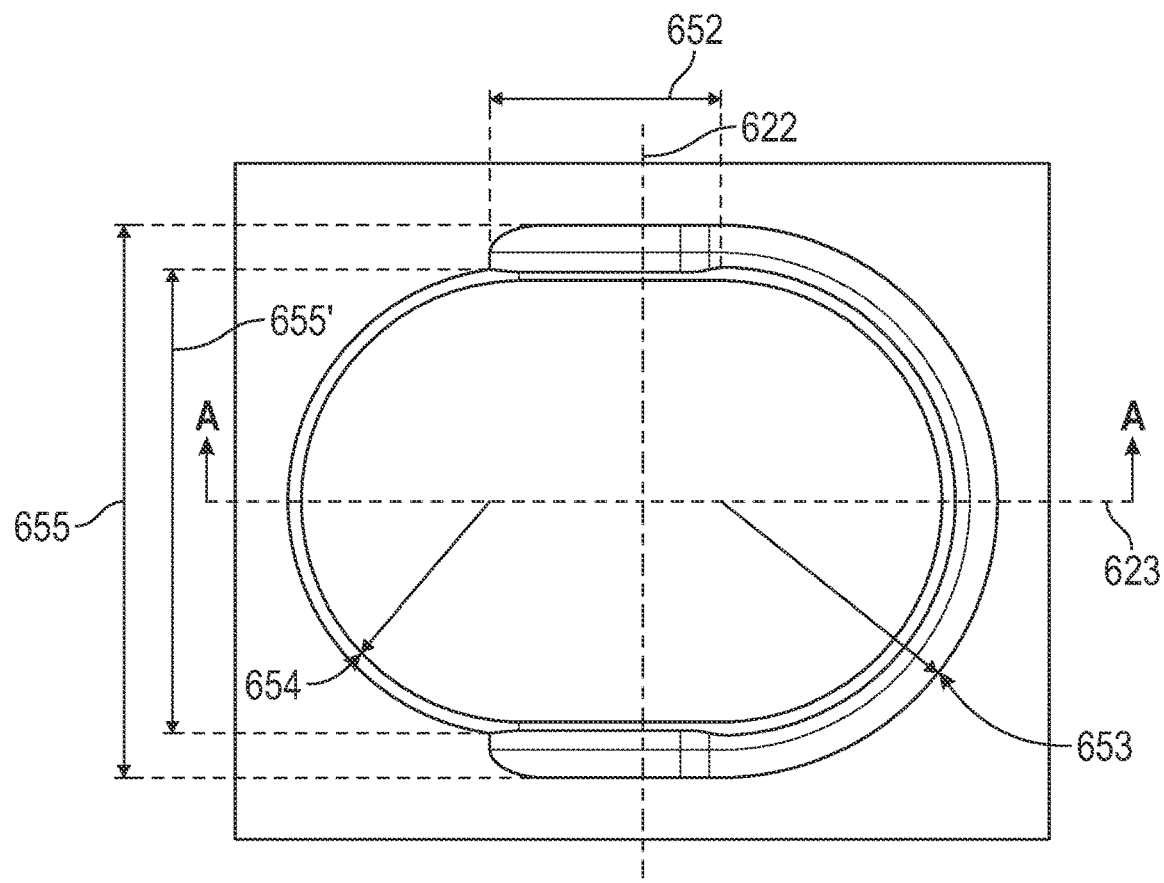
Figure 6M:
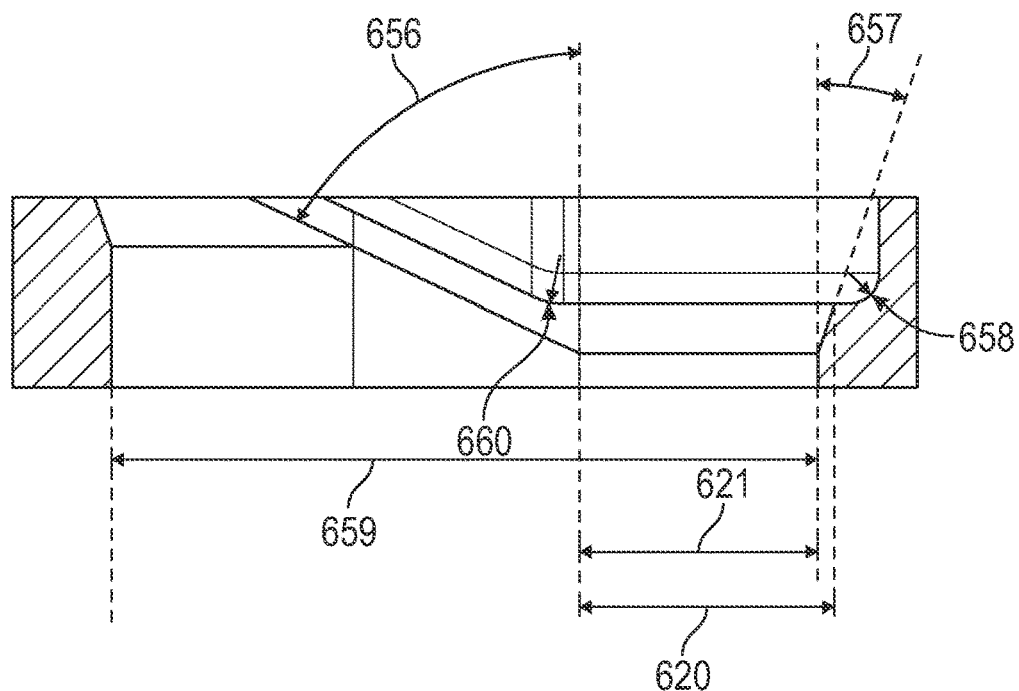

Various embodiments include various components. An embodiment may include an anchor while another embodiment may include a plate. Another embodiment may include the tool of FIG. 7A. Still other embodiments include kits that may be sent to a destination, such as a hospital, clinic, or warehouse. An embodiment includes the plate of FIG. 6A as well as the anchor of FIG. 6A. The bone anchor includes a head and a body, the head being coupled to the body. The head is threaded with a thread and the thread is configured to deform the second curved surface to lock the bone anchor to the plate. See, for example, FIG. 6K showing in phantom the overlap between anchor and plate (and therefore the amount of deformation to either or both of the plate and the anchor). This deformation locks the anchor to the plate to prevent the anchor from backing out and away from the plate.

In an embodiment, the aperture includes a minimum diameter, the bone anchor includes a maximum diameter, and the maximum diameter is greater than the minimum diameter. For example, the width of the anchor head may be wider than width 655' but not as wide as width 655. The bone anchor is configured to move along the first surface 610 and towards both the second plate surface 603 and the second outer sidewall 605 when: (a) the anchor thread contacts the first surface, and (b) the bone anchor is rotated about a long axis of the bone anchor.

As can be seen in the embodiment of FIGS. 6A-6M, the aperture 606 is unthreaded. Further, the aperture defines a profile where the aperture interfaces the first plate surface and the profile is non-circular. Further, the unthreaded aperture is configured for polyaxial fixation with a thread of the bone anchor. Some or all of this arrangement promotes ease of anchor translation across and down the plate, length of anchor translation, and/or locking of threaded anchors to the aperture.

Unlike conventional systems, the aperture 606 does not include a bushing or a ring that is not monolithic with the plate. Further, all of the first and second surfaces, the first and second plate surfaces, and the first and second outer sidewalls are monolithic with one another. Some or all of these features result in an ease of manufacture, ease of sterilization, and/or increased reliability of operation of the system.

As used herein, a bushing includes a type of bearing and may include a cylindrical lining designed to reduce friction and wear inside a hole (e.g., a casing for a shaft, pin or hinge). As used herein, a plane is a flat, two-dimensional surface that extends infinitely far. A plane is the two-dimensional analogue of a point (zero dimensions), a line (one dimension) and three-dimensional space. In a Euclidean space of any number of dimensions, a plane is uniquely determined by any of the following: (a) three non-collinear points (points not on a single line), (b) a line and a point not on that line, (c) two distinct but intersecting lines, or (d) two parallel lines.

Plate 600 may be modified to take on elements of the embodiments of FIGS. 2A-C. For example, in an embodiment the aperture 606 includes one of a counterbore or a countersink. The first and second plate surfaces include first and second openings into the aperture. Further, (a) no portion of the aperture is threaded; (b) the aperture includes a curved inner wall and the curved inner wall includes reliefs along its perimeter; (c) measured orthogonal to the long axis, the second opening is wider than the first opening, and (d)

measured parallel to the long axis, the reliefs are further from the first opening than the second opening.

In an embodiment, the reliefs are collectively configured such that threads of the bone anchor deform the landing adjacent at least one of the reliefs when the bone anchor mates with the plate. Also, the bone anchor and the reliefs are collectively configured to lock the bone anchor to the plate in response to the threads of the bone anchor head deforming the landing.

In an embodiment, plate 600 is a compression plate. As used herein, a compression plate includes a plate that has screw holes having an inclination such that as the screw is tightened, the screw head slides down this inclination, thereby compressing the fracture. This concept is predicated on eccentric ("away from" fracture) screw placement within the plate hole, as well as, anchoring the plate first with another screw on the opposite side of the fracture.

Dimension 652 controls the amount of translation (left to right in the case of FIG. 6L) that the screw can achieve. In an embodiment, dimension 652 allows for a minimum translation of 2 mm (horizontal translation) but other embodiments allow for translations of up to 2.5 mm or more. Dimension 652 is measured by the distance between the centers of the two opposing circles (i.e., the circle that forms surface 616 and the circle that forms surface 662).

Dimension 653 allows for the mating of both locking and non-locking anchors. This feature allows the anchors to advance axially down the hole. In various embodiments the feature ranges from 1.6 mm to 7.00 mm.

The diameter or radius 654 of the through hole (see lower edge of chamfered surface 616) allows for the anchor to pass through the through hole without interference. In an embodiment this feature ranges from 1.2 mm to 7.0 mm.

Dimension 655 defines the width of the upper channel or ramp and allows for contact with both locking and non-locking screws and promotes translation of anchors across the eccentric hole. Making the width larger than the width of the locking anchor helps ensure the anchor will translate when rotated or screwed into the plate. In an embodiment width 655 is at least 15% greater than the anchor head.

Dimension 656 is somewhat dependent on dimension 652. Angle 656 ensures the anchor translates across the hole. If the angle is too steep, the amount of translation may be prematurely terminated. Additionally, if the angle is to large, there may be no translation at all. In an embodiment the angle ranges from 90 degrees to 30 degrees. In an embodiment the angle is 65 degrees.

Dimension 657 relates to the degree of chamfer at various locations such as surface 616. This degree allows an anchor to more easily transition from the top surface of the plate to the eccentric hole ramp.

Dimension 658 may be indicative of the counterbore formation process. Further, it helps create the resulting lip that the locking anchor can deform (see FIG. 6k) causing the screw to lock. In an embodiment dimension 658 is around 0.010" but in other embodiments is between 0.005" and 0.015".

Dimension 659 is a result of diameters of the two adjoining holes that cooperate to form aperture 606. Having dimension 659 adequately proportioned helps achieve a goal of 2 mm of compression/translation.

Dimension 660 is a ramp feature that allows the continued transition of the anchor. Without the radius, the anchor may not translate fully across the hole. An embodiment includes a radius of 0.025" but other embodiments range from 0.01" to 0.5".

Attention now turns to the embodiments of FIGS. 7A-7H. In many cases a physician may wish to manipulate a plate in various manners. For example, the physician may wish to place the plate in various locations and then, having decided on a location for permanent fixation, use the plate as a guide to drill pilot holes and the like. Sometimes specialized tools are used to affix to the plates to aid the physician in these operations. Conventional tools may interface with the plate via mating threads or springs (or other compressible mechanisms). However, doing so may alter (e.g., deform) the threads on the plate (or other parts of the plate) and/or components of the tool itself (leading to premature degradation of the tool such that a new tool must be acquired). However, embodiments of FIGS. 7A-7H address these shortcomings with a tool that interfaces the plate in a locking fashion without deformation of the instrument or the implant, thereby allowing for repeated use without the concern of wear.

FIGS. 7A-7H disclose an embodiment of a bone fixation system comprising a plate 151 (see FIGS. 2A-C for more details regarding an embodiment of the plate) and a tool 701. As described above with regard to FIGS. 2A-C, the plate includes an aperture 152 configured to receive a bone anchor. The aperture includes a long axis 153 that traverses the aperture but does not intersect the plate. The aperture includes a first opening 154 and a second opening 155. The aperture includes a plate projection 156 and the plate projection projects inwardly from a wall of the aperture and towards the long axis. The plate projection has a first surface 158 and a second surface 159, and the plate projection includes a number of plate reliefs 165, 167 along its perimeter.

The tool includes a post 714 having proximal and distal ends. The distal end includes a number of tool projections 702, 703. The number of tool projections is not greater than the number of plate reliefs and each tool projection is configured to mate with one of the plate reliefs.

Specifically, the plate reliefs include first and second plate reliefs 165, 167 and the tool includes: (a) first and second tool projections 702, 703, and (b) first and second sloped surfaces 705, 706. The first sloped surface directly connects to the first tool projection and the second sloped surface directly connects to the second tool projection. The first sloped surface forms a first ramp 707 that thickens as the first slope surface advances away from the distal end of the tool and towards the proximal end of the tool.

As shown in FIGS. 7B, 7C, and 7D, the tool engages the plate shelf. Lobes on the tool pass through the reliefs on the plate shelf. Then the tool is rotated and tool ramps drive the plate shelf up against a ledge on the tool. This creates a resistance fit to secure the plate without having to resort to threads or resilient members such as springs and the like.

The tool includes a third tool projection 704. This projection could be considered a ledge, shelf, undercut, and the like. The third tool projection is proximal to the first tool projection. The tool includes a void 708 that is between a distal edge of the third tool projection and a proximal edge of the first tool projection. The plate projection has a plate projection thickness 186 between the first and second surfaces of the plate projection. The plate projection thickness is measured parallel to the long axis of the aperture. The void has a void thickness 709 measured parallel to a long axis of the tool and from the distal edge of the third tool projection to the proximal edge of the first tool projection. The void thickness is less than the plate projection thickness. Based on the void thickness being less than the plate projection thickness, the void is configured to fixedly secure the plate projection via a resistance fit of the plate projection between the first and third tool projections. More generally, a resistance fit is made to secure the plate to the tool. However, the resistance fit is such that any deformation to plate or tool is minimal or clinical insignificant.

Distance 710 extends parallel to the long axis of the tool and from the distal edge of the third tool projection to the distal end of the tool. The distance is greater than the plate projection thickness.

A first distance 711 extends parallel to the long axis of the tool and from the distal edge of the third tool projection to a first location on the first sloped surface. The first distance is equal to the plate projection thickness. This is where interference or the resistance fit begins. A second distance extends parallel to the long axis of the tool and from the distal edge of the third tool projection to a second location on the first sloped surface. The second distance is greater than the plate projection thickness. The second distance may just be measured from slightly further down the ramp towards the distal end of the tool.

In embodiment the post includes a hollow conduit 712 that extends from a proximal end of the tool to a distal end of the tool. A physician may use the conduit to serve as a drill guide for pilot hole creation and the like.

In an embodiment, the number of tool projections equals the number of plate reliefs. However, in other embodiments the number of tool projections may be less than the number of plate reliefs. In other embodiments the number of tool projections may equal one.

In an embodiment a first circular circumference 715 is included in a plane that is orthogonal to the long axis of the tool. The first circular circumference contacts an outermost tip of the first tool projection and an outermost tip of the second tool projection. The first circular circumference has a first maximum diameter 713. A second circular circumference is included in a plane that is orthogonal to the long axis of the aperture. The second circular circumference contacts an outermost tip of the first plate relief projection and an outermost tip of the second plate relief. The second circular circumference has a second maximum diameter (the combination of 166+168). The second maximum diameter is greater than the first maximum diameter. As a result, the distal tip of the tool can pass through the plate aperture.

A third circular circumference is included in a plane that is orthogonal to the long axis of the aperture. The third circular circumference contacts an innermost edge of the first plate relief and an innermost edge of the second plate relief. The third circular circumference has a third maximum diameter (2*164 or 164+164). The third maximum diameter is less than the first maximum diameter. As a result, once the distal tip of the tool passes through the plate aperture, the distal tip can be rotated and then used to create a resistance fit between the plate and tool.

The first tool projection is proportioned to pass through the first plate relief when the tool is being fixed to the plate. For example, dimensions 703, 713, 705 are proportioned to allow the lobes to pass through the plate shelf reliefs.

As mentioned above, the plate includes no threads between the first and second openings and the plate includes no resilient members between the first and second openings. This allows an anchor to lock in a polyaxial manner. The first opening directly interfaces a first outer surface of the plate and the second opening directly interfaces a second outer surface of the plate. The first outer surface of the plate opposes the second outer surface of the plate.

The first opening has a first maximum diameter that is orthogonal to the long axis of the aperture; the second opening has a second maximum diameter that is orthogonal to the long axis of the aperture; and the second maximum diameter is greater than the first maximum diameter. This provides advantages regarding the amount of polyaxial variance between the anchor and plate.

In an embodiment (a) no portion of the aperture is threaded; (b) measured orthogonal to the long axis of the aperture, the second opening is wider than the first opening, and (c) measured parallel to the long axis of the aperture, the plate reliefs are further from the first opening than the second opening. This arrangement provides advantages in the amount of polyaxial variance between the anchor and plate and the ability to gain a low profile for the screw head with regard to the upper surface of the plate once the anchors are fully seated in the plate.

The tool, plate, and anchors may be packaged alone or together in various combinations. For example, the tool may be included in a kit with the plate and the anchor. The bone anchor and the plate reliefs may be collectively configured such that threads of the bone anchor head deform the first surface adjacent at least one of the plate reliefs when the bone anchor mates with the plate. The bone anchor and the plate reliefs are collectively configured to lock the bone anchor to the plate in response to the threads of the bone anchor head deforming the first surface.

The proximal end of the tool functions as a user interface. The interface could be in many forms and may include the same diameter as the shank or post 714. Various embodiments include channels, knurls, rough coatings, and the like to facilitate ease of use. The length of the feature can be, in an embodiment, between 6" to 0.100". The transition between the user interface and post 714 can be, for example, a single piece with a radius or an interface that contains two bodies joined via a thread or interference fit. The shank or post 714 is shown with a consistent radius but other embodiments can be variable in diameter and could contain threads or other features that would interface with an outrigger system or additional instrumentation. In various embodiments, the length of feature 714 is between 6" to 0.100".

Dimension 703 relates to lobe size for the lobe or lobes that interfaces with the voids present in the locking hole. The width of the projections/lobes need to be smaller than the voids in then locking hole. In an embodiment dimension 703 is 0.032" but in other embodiments is 0% to 50% less than the size of the void in the locking hole. A singular or plurality of projections are possible while in some embodiments the number of lobes equals the number of voids in the locking hole.

Dimension 704 should be proportioned such that embodiments with such a ring fit without interference through the aperture of the locking hole. An embodiment has a diameter of 0.150" but the diameter can be smaller in other embodiments. In such other embodiments, the wall thickness between the inner and outer wall, if cannulated, is greater than 0.04".

Dimension 705 provides a lobe breakout radius. If the radius is too big, it will interfere with the void of the locking hole. In an embodiment the dimension is 0.015" but in other embodiments the dimension is between 0.001" and 0.030".

Dimension 713 addresses the effective diameter that the projections make when extrapolating the diameter for the maximum heights ensures that the projects overlap the aperture. In an embodiment dimension 713 overlaps the inner diameter of the plate (2*radius 164) by between 1% and 7%.

Dimension 711 is the distance between the ledge 704 (which interfaces with the top surface of the plate shelf) and the point at which interference starts on the lower surface of the plate shelf. In an embodiment this value is equal to the distance 186 between the two surfaces 158, 159. In an embodiment another location on the ramped surface is 0-50% larger than the distance 186 between the two surfaces.

The angle of inclination for the ramped surface 705 allows for the device to wedge onto the locking hole surfaces without damage. Additionally, it facilitates a "locking" tower whose locking is not based on interfacing threads or a spring mechanism. For an embodiment the angle is 15 degrees but in other embodiments is between 7.5 to 25 degrees.

Dimension 710 defines the distance from the distal end of the tool to where the shelf 704 interfaces with the first surface 158 of the projection on the locking hole. In an embodiment this distance is long enough to extend past the second surface 159 of the projection of the locking hole to allow for the proper interface. Additionally, this distance includes the thickness of the projections/lobes 702, 703. The thickness of projections/lobes 702, 703 is, in some embodiments, between 0.010" to 0.100".

Dimension 709 is the distance between the shelf 704 that interfaces with the first surface 158 of the locking hole and the top of a lobe. In an embodiment this is smaller than the distance 186 between the two surfaces. In an embodiment, the distance is 0-50% smaller than the distance 186 between the two surfaces. This promotes the resistance fit between the plate and tool.

In addition, forming a relief behind the lobes helps ensure there is no or little interference between the instruments and the locking hole (other than the projections 702, 703).

Figure 7H:
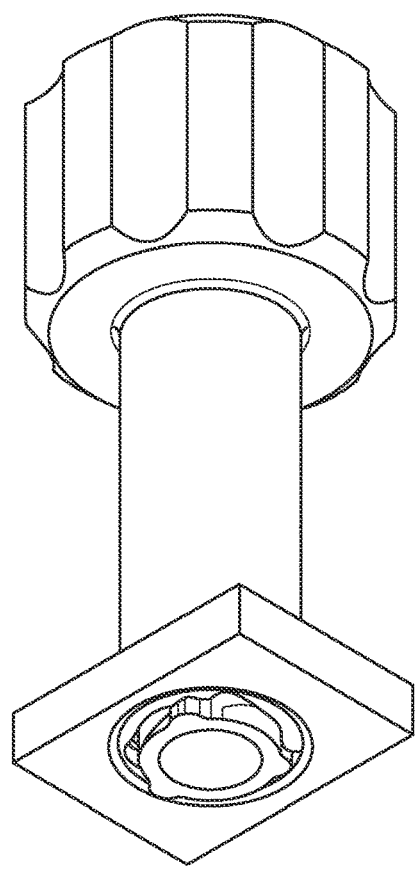

FIG. 7H shows an assembly of the instrument and plate showing the two components engaged or "locked". A physician may use this device as a drill guide and as a plate positioner because the cannulation in the instrument accepts drills of certain diameters. Additionally, because the instrument locks into the plate, it can be used to spatially control the plate.

Embodiments have been shown with threaded anchors however plates addressed herein may also operate with partially threaded anchors and/or non-threaded anchors. Plates may include combinations of apertures. For example, a single plate may include the embodiments of FIGS. 2A and 6A. For the embodiment of FIG. 6A, the plate may provide locking and compression for threaded anchors (with threaded heads) and compression for anchors without threaded heads.

The following examples pertain to further embodiments.

Example 1. A bone fixation system comprising: a bone anchor; and a plate; wherein the bone anchor: (a)(i) includes a head and a body, the head being coupled to the body, (a)(ii) has a long axis, (a)(iii) the body has an outer diameter that is orthogonal to the long axis and the head has an outer diameter that is orthogonal to the long axis, and (a)(iv) the outer diameter of the head is greater than the outer diameter of the body; wherein: (b)(i) the plate includes an aperture, (b)(ii) the aperture includes a long axis that traverses the aperture but does not intersect the plate, (b)(iii) the aperture includes a first opening and a second opening, (b)(iv) the aperture includes a projection and the projection projects inwardly from a wall of the aperture and towards the long axis, (b)(v) the projection has a first surface and a second surface, and (b)(vi) at least a portion of the first surface is coplanar with a first plane, and (b)(vii) the first plane intersects the long axis at a first angle and the first angle is between 85 degrees and 95 degrees.

In an embodiment such a bone anchor may include what some call a "headless" screw. Such a screw may have varying pitch or lead (e.g., a larger pitch or lead near the distal end and a smaller pitch or lead near the proximal end). However, the screw may still taper to some extent, even if the taper near the proximal end is slight.

Example 2. The bone fixation system of example 1 wherein: the projection includes an inner wall that couples the first surface of the projection to the second surface of the projection; the inner wall of the projection has a first portion that is a first distance from the long axis, the first distance being orthogonal to the long axis; the inner wall of the projection has a second portion that is a second distance from the long axis, the second distance being orthogonal to the long axis; the second distance is greater than the first distance.

Example 3. The bone fixation system of example 2 wherein: the inner wall of the projection has a third portion that is a third distance from the long axis, the third distance being orthogonal to the long axis; the third distance is greater than the first distance.

Example 4. The bone fixation system of example 3 wherein: the third distance is greater than the second distance; the second distance is measured from a location of the second portion that is furthest from the long axis as compared to other locations of the second portion; the third distance is measured from a location of the third portion that is furthest from the long axis as compared to other locations of the third portion.

Example 5. The bone fixation system of example 3 wherein: the inner wall of the projection defines an inner perimeter of the projection; the inner wall of the projection has a fourth portion that is the first distance from the long axis; the first portion is between the second and third portions; the third portion is between the first and fourth portions.

Example 6. The bone fixation system of example 2 wherein the first plane is orthogonal to the long axis.

Example 7. The bone fixation system of example 1 wherein the first plane is orthogonal to the long axis.

Example 8. The bone fixation system of example 1 wherein at least a portion of the second surface is coplanar with a second plane, and (b)(viii) the second plane intersects the long axis at a second angle and the second angle is between 85 degrees and 95 degrees.

Example 9. The bone fixation system of example 8 wherein the second plane is orthogonal to the long axis.

Example 10. The bone fixation system of example 8 wherein the first plane is orthogonal to the long axis.

Example 11. The bone fixation system of example 1 wherein: the first surface is between the second surface and the first opening; the second surface is between the first surface and the second opening; the first surface is a first distance from the first opening, the first distance being parallel to the long axis; the second surface is a second distance from the second opening, the second distance being parallel to the long axis; the first distance is greater than the second distance.

Example 12. The bone fixation system of example 1 wherein: the plate includes no threads between the first and second openings; the first opening directly interfaces a first outer surface of the plate; the second opening directly interfaces a second outer surface of the plate; the first outer surface of the plate opposes the second outer surface of the plate.

Example 13. The bone fixation system of example 12 wherein: the first opening has a first maximum diameter that is orthogonal to the long axis; the second opening has a second maximum diameter that is orthogonal to the long axis; the second maximum diameter is greater than the first maximum diameter.

Example 14. The bone fixation system of example 13 wherein: the head of the bone anchor includes a third maximum diameter; the first maximum diameter is greater than the third maximum diameter; the projection forms a ring that circumnavigates an inner portion of the aperture; the ring has a minimum diameter; the minimum diameter of the ring is less than the third maximum diameter.

Example 15. The bone fixation system of example 1 wherein: at least a portion of the head of the bone anchor is included in a proximal-most fifth of the bone anchor; the portion of the head of the bone anchor includes threads.

Example 16. The bone fixation system of example 15 wherein: the body of the bone anchor includes threads; the threads of the body of the bone anchor have a first thread height; the threads of the portion of the head of the bone anchor have a second thread height; the second thread height is less than the first thread height.

Example 17. The bone fixation system of example 16 wherein: the threads of the body of the bone anchor have a first crest width; the threads of the portion of the head of the bone anchor have a second crest width; the second crest width is greater than the first crest width.

Example 18. The bone fixation system of example 1 wherein the projection forms a ring that circumnavigates an inner portion of the aperture.

Example 19. The bone fixation system of example 1 wherein: the head of the bone anchor has a circular cross-section, the cross-section being orthogonal to the long axis of the bone anchor; the outer diameter of the head is greater than the outer diameter of the body based on the bone anchor including a tapered portion; the tapered portion includes a thread root that tapers outwardly at an angle between 10 degrees and 25 degrees; the head of the bone anchor includes a maximum diameter taken orthogonal to the long axis of the bone screw; the projection forms a ring that circumnavigates an inner portion of the aperture, the ring including a minimum diameter; the maximum diameter of the head of the bone anchor is between 5 percent and 10 percent larger than the minimum diameter of the ring; at least a portion of the head of the bone anchor is included in a proximal-most fifth of the bone anchor, the portion of the head of the bone anchor including threads; the threads of the portion of the head of the bone anchor have a thread height, the thread height being between 0.0254 mm and 0.3048 mm; the threads of the portion of the head of the bone anchor have a crest width, the crest width being between 0.0508 mm and 0.3048 mm; the first surface is between the second surface and the first opening and the second surface is between the first surface and the second opening; the first surface is a first distance from the first opening, the first distance being parallel to the long axis and being between 0.254 mm and 1.27 mm; the projection includes an inner wall that couples the first surface of the projection to the second surface of the projection; the inner wall of the projection has a first portion that is a second distance from the long axis, the second distance being orthogonal to the long axis; the inner wall of the projection has a second portion that is a third distance from the long axis, the third distance being orthogonal to the long axis; the third distance is greater than the second distance and the third distance is between 0.508 mm and 1.016 mm; the third distance is greater than the second distance by a differential distance and the differential distance is between 0.127 mm and 0.381 mm; the first surface is a fourth distance from the second surface, the fourth distance being parallel to the long axis and being between 0.254 mm and 5.588 mm; the first portion of the projection projects inwardly from the wall of the aperture and towards the long axis by a fifth distance, the fifth distance being between 0.254 mm and 0.127 mm.

Example 19.5 The bone fixation system of example 19 wherein the threads of the portion of the head of the bone anchor include thread crests that taper outwardly at an angle between 10 degrees and 20 degrees.

Example 20. A bone fixation system comprising: a bone anchor with a tapered head, the head being threaded; and a plate that includes a void, the void including one of a counterbore or a countersink; wherein: no portion of the void is threaded; the void includes an inner wall; the inner wall includes reliefs along its perimeter;

Example 21. The bone fixation system of example 20 wherein: the void includes the counterbore; the counterbore includes a landing, the landing including a surface that is defined by a plane; the plane is orthogonal to a long axis of the void; the counterbore includes a sidewall, the sidewall extending parallel to the long axis of the void.

Example 22. The bone fixation system of example 20 wherein: the bone anchor includes a material; the plate includes the material; the bone anchor is monolithic; the plate is monolithic.

Example 23. The bone fixation system of example 21 wherein: the bone anchor and the reliefs are collectively configured such that threads of the bone anchor head deform the landing adjacent at least one of the reliefs when the bone anchor mates with the plate; the bone anchor and the reliefs are collectively configured to lock the bone anchor to the plate in response to the threads of the bone anchor head deforming the landing.

Example 24. The bone fixation system of example 23 wherein the plate includes no resilient members.

For example, some conventional techniques may use a wire (e.g., nickel-chrome alloy with shape memory) that moves laterally while a screw is being inserted and then snaps back medially and over the screw head to prevent screw backout. However, no such resilient member is included in an embodiment of the plate.

Example 25. A bone fixation kit comprising: a plate that includes a void, the void including one of a counterbore or a countersink; wherein: the plate includes no resilient members; no portion of the void is threaded; the void includes an inner wall; the inner wall includes reliefs along its perimeter; the reliefs are configured such that threads of a bone anchor head will deform the inner wall adjacent at least one of the reliefs when the bone anchor mates with the plate.

Example 26. The bone fixation kit of example 25 wherein: the void includes the counterbore; the counterbore includes a landing, the landing including a surface that is defined by a plane; the plane is orthogonal to a long axis of the void; the counterbore includes a sidewall, the sidewall extending parallel to the long axis of the void.

Example 27. The bone fixation kit of example 25 comprising the bone anchor.

Example 5a. The bone fixation system according to any of examples 3-4 wherein: the inner wall of the projection defines an inner perimeter of the projection; the inner wall of the projection has a fourth portion that is the first distance from the long axis; the first portion is between the second and third portions; the third portion is between the first and fourth portions.

Example 6a. The bone fixation system according to any of examples 1-5 wherein the first plane is orthogonal to the long axis.

Example 8a. The bone fixation system according to any of examples 1-6 wherein at least a portion of the second surface is coplanar with a second plane, and (b)(viii) the second plane intersects the long axis at a second angle and the second angle is between 85 degrees and 95 degrees.

Example 10a. The bone fixation system according to any of examples 1-9 wherein the first plane is orthogonal to the long axis.

Example 11a. The bone fixation system according to any of examples 1-10 wherein: the first surface is between the second surface and the first opening; the second surface is between the first surface and the second opening; the first surface is a first distance from the first opening, the first distance being parallel to the long axis; the second surface is a second distance from the second opening, the second distance being parallel to the long axis; the first distance is greater than the second distance.

Example 12a. The bone fixation system according to any of examples 1-11 wherein: the plate includes no threads between the first and second openings; the first opening directly interfaces a first outer surface of the plate; the second opening directly interfaces a second outer surface of the plate; the first outer surface of the plate opposes the second outer surface of the plate.

Example 15a. The bone fixation system according to any of examples 1-14 wherein: at least a portion of the head of the bone anchor is included in a proximal-most fifth of the bone anchor; the portion of the head of the bone anchor includes threads.

Example 18a. The bone fixation system according to any of examples 1-17 wherein the projection forms a ring that circumnavigates an inner portion of the aperture.

Example 19a. The bone fixation system according to any of examples 1-18 wherein: the head of the bone anchor has a circular cross-section, the cross-section being orthogonal to the long axis of the bone anchor; the outer diameter of the head is greater than the outer diameter of the body based on the bone anchor including a tapered portion; the tapered portion includes a thread root that tapers outwardly at an angle between 10 degrees and 20 degrees; the head of the bone anchor includes a maximum diameter taken orthogonal to the long axis of the bone screw; the projection forms a ring that circumnavigates an inner portion of the aperture, the ring including a minimum diameter; the maximum diameter of the head of the bone anchor is between 5 percent and 10 percent larger than the minimum diameter of the ring; at least a portion of the head of the bone anchor is included in a proximal-most fifth of the bone anchor, the portion of the head of the bone anchor including threads; the threads of the portion of the head of the bone anchor have a thread height, the thread height being between 0.0254 mm and 0.3048 mm; the threads of the portion of the head of the bone anchor have a crest width, the crest width being between 0.0508 mm and 0.3048 mm; the first surface is between the second surface and the first opening and the second surface is between the first surface and the second opening; the first surface is a first distance from the first opening, the first distance being parallel to the long axis and being between 0.254 mm and 1.27 mm; the projection includes an inner wall that couples the first surface of the projection to the second surface of the projection; the inner wall of the projection has a first portion that is a second distance from the long axis, the second distance being orthogonal to the long axis; the inner wall of the projection has a second portion that is a third distance from the long axis, the third distance being orthogonal to the long axis; the third distance is greater than the second distance and the third distance is between 0.508 mm and 1.016 mm; the third distance is greater than the second distance by a differential distance and the differential distance is between 0.127 mm and 0.381 mm; the first surface is a fourth distance from the second surface, the fourth distance being parallel to the long axis and being between 0.254 mm and 5.588 mm; the first portion of the projection projects inwardly from the wall of the aperture and towards the long axis by a fifth distance, the fifth distance being between 0.254 mm and 0.127 mm.

Example 22a. The bone fixation system according to any of examples 20-21 wherein: the bone anchor includes a material; the plate includes the material; the bone anchor is monolithic; the plate is monolithic.

As used herein, monolithic means formed of a single unit. For example, the plate may be formed by forging, machining of a block of material, additive manufacturing, and the like. Such a unit would not include welds or portions joined via adhesives.

Example 23a. The bone fixation system according to any of examples 20-22 wherein: the bone anchor and the reliefs are collectively configured such that threads of the bone anchor head deform the landing adjacent at least one of the reliefs when the bone anchor mates with the plate; the bone anchor and the reliefs are collectively configured to lock the bone anchor to the plate in response to the threads of the bone anchor head deforming the landing.

Example 24a. The bone fixation system according to any of examples 20-23 wherein the plate includes no resilient members.

Example 27a. The bone fixation kit according to any of examples 25-26 comprising the bone anchor.

Example 6a'. The bone fixation system according to any of examples 5a wherein the first plane is orthogonal to the long axis.

Example 8a'. The bone fixation system according to any of examples 5a-6a wherein at least a portion of the second surface is coplanar with a second plane, and (b)(viii) the second plane intersects the long axis at a second angle and the second angle is between 85 degrees and 95 degrees.

Example 10a'. The bone fixation system according to any of examples 5a, 6a, 8a wherein the first plane is orthogonal to the long axis.

Example 11a'. The bone fixation system according to any of examples 5a, 6a, 8a, 10a wherein: the first surface is between the second surface and the first opening; the second surface is between the first surface and the second opening; the first surface is a first distance from the first opening, the first distance being parallel to the long axis; the second surface is a second distance from the second opening, the second distance being parallel to the long axis; the first distance is greater than the second distance.

Example 12a'. The bone fixation system according to any of examples 5a, 6a, 8a, 10a, 11a wherein: the plate includes no threads between the first and second openings; the first opening directly interfaces a first outer surface of the plate; the second opening directly interfaces a second outer surface of the plate; the first outer surface of the plate opposes the second outer surface of the plate.

Example 15a'. The bone fixation system according to any of examples 5a, 6a, 8a, 10a, 11a, 14a wherein: at least a portion of the head of the bone anchor is included in a proximal-most fifth of the bone anchor; the portion of the head of the bone anchor includes threads.

Example 18a'. The bone fixation system according to any of examples 5a, 6a, 8a, 10a, 11a, 14a, 17a wherein the projection forms a ring that circumnavigates an inner portion of the aperture.

Example 19a'. The bone fixation system according to any of examples 5a, 6a, 8a, 10a, 11a, 14a, 17a, 18a wherein: the head of the bone anchor has a circular cross-section, the cross-section being orthogonal to the long axis of the bone anchor; the outer diameter of the head is greater than the outer diameter of the body based on the bone anchor including a tapered portion; the tapered portion includes a thread root that tapers outwardly at an angle between 10 degrees and 20 degrees; the head of the bone anchor includes a maximum diameter taken orthogonal to the long axis of the bone screw; the projection forms a ring that circumnavigates an inner portion of the aperture, the ring including a minimum diameter; the maximum diameter of the head of the bone anchor is between 5 percent and 10 percent larger than the minimum diameter of the ring; at least a portion of the head of the bone anchor is included in a proximal-most fifth of the bone anchor, the portion of the head of the bone anchor including threads; the threads of the portion of the head of the bone anchor have a thread height, the thread height being between 0.0254 mm and 0.3048 mm; the threads of the portion of the head of the bone anchor have a crest width, the crest width being between 0.0508 mm and 0.3048 mm; the first surface is between the second surface and the first opening and the second surface is between the first surface and the second opening; the first surface is a first distance from the first opening, the first distance being parallel to the long axis and being between 0.254 mm and 1.27 mm; the projection includes an inner wall that couples the first surface of the projection to the second surface of the projection; the inner wall of the projection has a first portion that is a second distance from the long axis, the second distance being orthogonal to the long axis; the inner wall of the projection has a second portion that is a third distance from the long axis, the third distance being orthogonal to the long axis; the third distance is greater than the second distance and the third distance is between 0.508 mm and 1.016 mm; the third distance is greater than the second distance by a differential distance and the differential distance is between 0.127 mm and 0.381 mm; the first surface is a fourth distance from the second surface, the fourth distance being parallel to the long axis and being between 0.254 mm and 5.588 mm; the first portion of the projection projects inwardly from the wall of the aperture and towards the long axis by a fifth distance, the fifth distance being between 0.254 mm and 0.127 mm.

Example 23a'. The bone fixation system according to any of examples 22a wherein: the bone anchor and the reliefs are collectively configured such that threads of the bone anchor head deform the landing adjacent at least one of the reliefs when the bone anchor mates with the plate; the bone anchor and the reliefs are collectively configured to lock the bone anchor to the plate in response to the threads of the bone anchor head deforming the landing.

Example 24a'. The bone fixation system according to any of examples 22a, 23a wherein the plate includes no resilient members.

Example 1b. A bone fixation system comprising: a plate (600) configured to mate with a bone anchor (601); wherein the plate includes: (a) first and second plate surfaces (602, 603) that oppose one another; (b) first and second outer sidewalls (604, 605) that oppose one another and which do not include either of the first or second plate surfaces; and (c) an aperture (606) that extends from the first plate surface to the second plate surface; wherein the aperture includes: (a) a long axis (607) that traverses the aperture but does not intersect the plate; (b) first and second inner sidewalls (608, 609) that oppose one another; wherein the first inner sidewall includes a first surface (610), and the first surface: (a) slopes away from the first plate surface and towards the second plate surface, (b) slopes away from the first outer sidewall and towards the second outer sidewall, and (d) is planar; wherein the first inner sidewall includes a second surface (611), and the second surface: (a) slopes away from the first plate surface and towards the second plate surface, (b) slopes away from the first outer sidewall and towards the second outer sidewall, and (d) is not co-planar with the first surface.

A dual ramp embodiment helps to ease translation of the anchor and ensure the anchor translates over the entire intended length of translation.

Example 2b. The bone fixation system of example 1b wherein the first surface is chamfered.

Example 3b. The bone fixation system of example 2b wherein the second surface is not chamfered.

Example 4b. The bone fixation system of example 3b wherein the plate includes a counterbore and the counterbore includes the second surface.

Example 5b. The bone fixation system of example 1b wherein: the first surface includes first and second sloped edges (612, 613) that oppose one another; the second sloped edge is between the first sloped edge and the second plate surface; the first sloped edge is a first distance (614) from the long axis and is measured orthogonal to the long axis; the second sloped edge is a second distance (615) from the long axis and is measured orthogonal to the long axis; the second distance is smaller than the first distance; the first and second distances are in a plane (622) that is parallel to the long axis and which intersects the long axis.

Example 6b. The bone fixation system of example 5b wherein the second surface has a curved portion.

Example 7b. The bone fixation system of example 6b wherein the second surface directly interfaces the first plate surface but not the second plate surface.

Example 8b. The bone fixation system of example 6b wherein the second inner sidewall includes an additional first surface (610'), and the additional first surface: (a) slopes away from the first plate surface and towards the second plate surface, (b) slopes away from the first outer sidewall and towards the second outer sidewall, and (d) is planar; wherein the second inner sidewall includes an additional second surface (611'), and the additional second surface: (a) slopes away from the first plate surface and towards the second plate surface, (b) slopes away from the first outer sidewall and towards the second outer sidewall, and (d) is not co-planar with the additional first surface.

Example 9b. The bone fixation system of example 8b wherein: the additional first surface includes additional first and second sloped edges (612', 613') that oppose one another; the additional second sloped edge is between the additional first sloped edge and the second plate surface; the additional first sloped edge is an additional first distance (614') from the long axis and is measured orthogonal to the long axis; the additional second sloped edge is an additional second distance (615') from the long axis and is measured orthogonal to the long axis; the additional second distance is smaller than the additional first distance; the additional first and second distances are in the plane.

Example 10b. The bone fixation system of example 9b wherein: an additional plane (623) intersects the long axis and is parallel to the long axis, the additional plane intersects the first and second outer walls; the first sloped edge is the first distance from the additional plane along a majority of an entire length of the first sloped edge; the additional first sloped edge is the additional first distance from the additional plane along a majority of an entire length of the additional first sloped edge.

Example 11b. The bone fixation system of example 10b comprising first and second curved surfaces (616, 617), wherein: the first curved surface couples the first surface to the additional first surface; the second curved surface couples the first surface to the additional first surface; the first curved surface is a third distance from the first plate surface; the second curved surface is a fourth distance from the first plate surface; the third distance is less than the fourth distance; the third and fourth distances are in the additional plane.

Example 12b. The bone fixation system of example 11b wherein: the second curved surface includes first and second curved edges (618, 619) that oppose one another; the second curved edge is between the first curved edge and the second plate surface; the first curved edge is a fifth distance (620) from the long axis and is measured orthogonal to the long axis; the second curved edge is a sixth distance (621) from the long axis and is measured orthogonal to the long axis; the sixth distance is smaller than the fifth distance; the fifth and sixth distances are in the additional plane.

Example 13b. The bone fixation system of example 12b comprising the bone anchor, wherein: the bone anchor includes a head and a body, the head being coupled to the body; the head is threaded with a thread; the thread is configured to deform the second curved surface to lock the bone anchor to the plate.

Example 14b. The bone fixation system of example 11b wherein the second curved surface does not directly connect with the second plate surface.

Example 15b. The bone fixation system of example 9b wherein: the first sloped edge is entirely linear and does not taper towards the additional first sloped edge; the second sloped edge is entirely linear and does not taper towards the additional second sloped edge.

Example 16b. The bone fixation system of example 1b, wherein: the aperture includes a minimum diameter; the bone anchor includes a maximum diameter; the maximum diameter is greater than the minimum diameter; and the bone anchor is configured to move along the first surface and towards both the second plate surface and the second outer sidewall when: (a) the thread contacts the first surface, and (b) the bone anchor is rotated about a long axis of the bone anchor.

Example 17b. The bone fixation system of example 16b, wherein: the aperture is unthreaded; the aperture defines a profile where the aperture interfaces the first plate surface and the profile is non-circular.

Example 18b. The bone fixation system of example 17b wherein the unthreaded aperture is configured for polyaxial fixation with a thread of the bone anchor.

Example 19b. The bone fixation system of example 1b, wherein: the aperture does not include a bushing; the aperture does not include a ring that is not monolithic with the plate; all of the first and second surfaces, the first and second plate surfaces, and the first and second outer sidewalls are monolithic with one another.

Example 20b. The bone fixation system of example 1b, wherein: the void includes one of a counterbore or a countersink; the first and second plate surfaces include first and second openings into the aperture; wherein: (a) no portion of the aperture is threaded; (b) the aperture includes a curved inner wall and the curved inner wall includes reliefs along its perimeter; (c) measured orthogonal to the long axis, the second opening is wider than the first opening, and (d) measured parallel to the long axis, the reliefs are further from the first opening than the second opening.

Example 21b. The bone fixation system of example 20b, wherein: the aperture includes the counterbore; the counterbore includes a landing, the landing including a surface that is defined by a plane; the plane is orthogonal to the long axis; the counterbore includes an additional sidewall portion (624), the additional sidewall portion extending parallel to the long axis.

Example 22b. The bone fixation system of example 20b wherein: the reliefs are collectively configured such that threads of the bone anchor deform the landing adjacent at least one of the reliefs when the bone anchor mates with the plate; the bone anchor and the reliefs are collectively configured to lock the bone anchor to the plate in response to the threads of the bone anchor head deforming the landing.

Example 23b. The bone fixation system of example 22b wherein the plate includes no resilient members.

Example 24b. The bone fixation system of example 21b wherein the plate is a compression plate.

Example 25b. A bone fixation system comprising: a plate (600) configured to mate with a bone screw (601); wherein the plate includes: (a) first and second outer sidewalls (604, 605); and (b) a hole (606) that extends from a first plate surface (602) to a second plate surface (603); wherein the hole includes: (a) a long axis (607) that does not intersect the plate; and (b) first and second inner sidewalls (608, 609); wherein the first inner sidewall includes a planar first ramp (610) that ramps down and away from the first plate surface and the first outer sidewall; wherein the first inner sidewall includes a second ramp (611) that: (a) ramps down and away from the first plate surface and the first outer sidewall, and (b) is not co-planar with the first ramp.

Example 26b. The bone fixation system of example 25b wherein: (a) the first ramp is chamfered, (b) the second ramp is not chamfered, (c) the plate is a compression plate, (d) the hole is unthreaded and non-circular, and (e) the hold includes no resilient members.

Example 27b. The bone fixation system of example 26b wherein the plate includes a counterbore and the counterbore includes the second ramp.

Example 28b. The bone fixation system of example 26b wherein the second ramp has a curved portion.

Example 29b. The bone fixation system of example 28b wherein the second ramp directly interfaces the first plate surface but not the second plate surface.

Example 30b. The bone fixation system of example 26b wherein the first ramp has an innermost edge and the innermost edge does not taper as the first ramp ramps down and away from the first plate surface and the first outer sidewall.

Example 31b. The bone fixation system of example 30b comprising the bone screw, wherein the bone screw has a threaded head configured to deform part of the plate to lock the bone screw to the plate.

Example 32b. The bone fixation system of example 30b, wherein the system is configured so the bone screw moves down the first ramp when: (a) a bone screw thread contacts the first ramp, and (b) the bone screw is rotated about a long axis of the bone screw.

Example 1c. A bone fixation system comprising: a plate (151); and a tool (701); wherein: (a) the plate includes an aperture (152) configured to receive a bone anchor, (b) the aperture includes a long axis (153) that traverses the aperture but does not intersect the plate, (c) the aperture includes a first opening (154) and a second opening (155), (d) the aperture includes a plate projection (156) and the plate projection projects inwardly from a wall of the aperture and towards the long axis, (e) the plate projection has a first surface (158) and a second surface (159), and (f) the plate projection includes a number of plate reliefs (165, 167) along its perimeter; wherein: (a) the tool includes a post (714) having proximal and distal ends, (b) the distal end includes a number of tool projections (702, 703), (c) the number of tool projections is not greater than the number of plate reliefs, (d) each tool projection is configured to mate with one of the plate reliefs.

Example 2c. The bone fixation system of example 1c, wherein: the plate reliefs include first and second plate reliefs (165, 167); the tool includes: (a) first and second tool projections (702, 703), (b) first and second sloped surfaces (705, 706), and (c) the first sloped surface directly connects to the first tool projection and the second sloped surface directly connects to the second tool projection.

Example 3c. The bone fixation system of example 2c, wherein the first sloped surface forms a first ramp (707) that thickens as the first slope surfaces advances away from the distal end of the tool and towards the proximal end of the tool.

Example 4c. The bone fixation system of example 3c, wherein the tool includes a third tool projection (704), wherein: the third tool projection is proximal to the first tool projection; the tool includes a void (708) that is between a distal edge of the third tool projection and a proximal edge of the first tool projection; the plate projection has a plate projection thickness (186) between the first and second surfaces of the plate projection, the plate projection thickness measured parallel to the long axis of the aperture; the void has a void thickness (709) measured parallel to a long axis of the tool and from the distal edge of the third tool projection to the proximal edge of the first tool projection; the void thickness is less than the plate projection thickness.

Example 5c. The bone fixation system of example 4c, wherein, based on the void thickness being less than the plate projection thickness, the void is configured to fixedly secure the plate projection via a resistance fit of the plate projection between the first and third tool projections.

Example 6c. The bone fixation system of example 5c, wherein: a distance (710) extends parallel to the long axis of the tool and from the distal edge of the third tool projection to the distal end of the tool; the distance is greater than the plate projection thickness.

Example 7c. The bone fixation system of example 5c, wherein: a first distance (711) extends parallel to the long axis of the tool and from the distal edge of the third tool projection to a first location on the first sloped surface; the first distance is equal to the plate projection thickness.

Example 8c. The bone fixation system of example 7c, wherein: a second distance extends parallel to the long axis of the tool and from the distal edge of the third tool projection to a second location on the first sloped surface; the second distance is greater than the plate projection thickness.

Example 9c. The bone fixation system of example 7c wherein the post includes a hollow conduit (712) that extends from a proximal end of the tool to a distal end of the tool.

Example 10c. The bone fixation system of example 9c, wherein the number of tool projections equals the number of plate reliefs.

Example 11c. The bone fixation system of example 9c, wherein: a first circular circumference (715) is included in a plane that is orthogonal to the long axis of the tool; the first circular circumference contacts an outermost tip of the first tool projection and an outermost tip of the second tool projection; the first circular circumference has a first maximum diameter (713); a second circular circumference is included in a plane that is orthogonal to the long axis of the aperture; the second circular circumference contacts an outermost tip of the first plate relief projection and an outermost tip of the second plate relief; the second circular circumference has a second maximum diameter (166, 168); the second maximum diameter is greater than the first maximum diameter.

Example 12c. The bone fixation system of example 11c, wherein: a third circular circumference is included in a plane that is orthogonal to the long axis of the aperture; the third circular circumference contacts an innermost edge of the first plate relief and an innermost edge of the second plate relief; the third circular circumference has a third maximum diameter (164, 164); the third maximum diameter is less than the first maximum diameter.

Example 13c. The bone fixation system of example 5c wherein the first tool projection is proportioned to pass through the first plate relief when the tool is being fixed to the plate.

Example 13c'. The bone fixation system according to any of examples 1c to 12c wherein the first tool projection is proportioned to pass through the first plate relief when the tool is being fixed to the plate.

Example 14c. The bone fixation system of example 5c wherein: the plate includes no threads between the first and second openings; the plate includes no resilient members between the first and second openings; the first opening directly interfaces a first outer surface of the plate; the second opening directly interfaces a second outer surface of the plate; the first outer surface of the plate opposes the second outer surface of the plate.

Example 14c'. The bone fixation system according to any of examples 1c to 13c wherein: the plate includes no threads between the first and second openings; the plate includes no resilient members between the first and second openings; the first opening directly interfaces a first outer surface of the plate; the second opening directly interfaces a second outer surface of the plate; the first outer surface of the plate opposes the second outer surface of the plate.

Example 15c. The bone fixation system of example 14c wherein: the first opening has a first maximum diameter that is orthogonal to the long axis of the aperture; the second opening has a second maximum diameter that is orthogonal to the long axis of the aperture; the second maximum diameter is greater than the first maximum diameter.

Example 16c. The bone fixation system of example 1c, wherein: (a) no portion of the aperture is threaded; (b) measured orthogonal to the long axis of the aperture, the second opening is wider than the first opening, and (c) measured parallel to the long axis of the aperture, the plate reliefs are further from the first opening than the second opening.

Example 16c'. The bone fixation system according to any of examples 1c to 14c, wherein: (a) no portion of the aperture is threaded; (b) measured orthogonal to the long axis of the aperture, the second opening is wider than the first opening, and (c) measured parallel to the long axis of the aperture, the plate reliefs are further from the first opening than the second opening.

Example 17c. The bone fixation system of example 16c wherein: the aperture includes a counterbore; the counterbore includes the first surface, the first surface being defined by a plane; the plane is orthogonal to the long axis of the aperture; the counterbore includes a sidewall, the sidewall extending parallel to the long axis of the aperture.

Example 18c. The bone fixation system of example 16c comprising the bone anchor, wherein: the bone anchor: (a) includes a head and a body, the head being coupled to the body, (b) has a long axis, (c) the body has an outer diameter that is orthogonal to the long axis and the head has an outer diameter that is orthogonal to the long axis, and (a)(iv) the outer diameter of the head is greater than the outer diameter of the body; the bone anchor and the plate reliefs are collectively configured such that threads of the bone anchor head deform the first surface adjacent at least one of the plate reliefs when the bone anchor mates with the plate; the bone anchor and the plate reliefs are collectively configured to lock the bone anchor to the plate in response to the threads of the bone anchor head deforming the first surface.

Example 19c. A bone fixation system comprising: a plate (151); and a tool (701); wherein: (a) the plate includes a hole (152) to receive a bone anchor, (b) the hole includes a shelf (156), (c) the shelf includes a number of recesses (165, 167); and (d) the hole is unthreaded and includes no resilient parts; wherein: (a) a distal end of the tool includes one or more lobes (702), (b) a number of lobes is no greater than the number of recesses, (c) each of the one or more lobes is configured to mate with one of the recesses.

Example 20c. The bone fixation system of example 19c, wherein: the tool includes a ramp (705) and a ledge (704); the ramp is configured to slide the shelf along the ramp and toward the ledge when the tool is being connected to the plate; the tool is configured to retain the shelf via a resistance fit of the shelf between the one or more lobes and the ledge.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a device side of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first structure "on" a second structure is directly on and in immediate contact with the second structure unless such is specifically stated; there may be a third structure or other structure between the first structure and the second structure on the first structure. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A bone fixation system comprising:
a plate; and
a tool;
wherein: (a) the plate includes an aperture configured to receive a bone anchor, (b) the aperture includes a long axis that traverses the aperture but does not intersect the plate, (c) the aperture includes a first opening and a second opening, (d) the aperture includes a plate projection and the plate projection projects inwardly from a wall of the aperture and towards the long axis, (e) the plate projection has a first surface and a second surface, and (f) the plate projection includes at least a first, second, and third plate reliefs along its perimeter;
wherein: (a) the tool includes a post having proximal and distal ends, (b) the distal end includes at least a first, second, and third tool projections, (c) a number of tool projections is not greater than a number of plate reliefs, (d) each tool projection is configured to mate with one of the plate reliefs; and (e) first and slope surfaces, wherein the first sloped surface directly connects to the first tool projection and the second sloped surface directly connects to the second tool projection;
wherein the first sloped surface forms a first ramp that thickens as the first slope surfaces advances away from the distal end of the tool and towards the proximal end of the tool;
wherein the third tool projection is proximal to the first tool projection; and
wherein the tool includes a void that is between a distal edge of the third tool projection and a proximal edge of the first tool projection;
the plate projection has a plate projection thickness between the first and second surfaces of the plate projection, the plate projection thickness measured parallel to the long axis of the aperture;
the void has a thickness measured parallel to a long axis of the tool and from the distal edge of the third tool projection to the proximal edge of the first tool projection; and the void thickness is less than the plate projection thickness.

2. The bone fixation system of claim 1, wherein, based on the void thickness being less than the plate projection thickness, the void is configured to fixedly secure the plate projection via a resistance fit of the plate projection between the first and third tool projections.

3. The bone fixation system of claim 2, wherein:
a distance extends parallel to the long axis of the tool and from the distal edge of the third tool projection to the distal end of the tool;
the distance is greater than the plate projection thickness.

4. The bone fixation system of claim 2, wherein:
a first distance extends parallel to the long axis of the tool and from the distal edge of the third tool projection to a first location on the first sloped surface;
the first distance is equal to the plate projection thickness.

5. The bone fixation system of claim 4, wherein:
a second distance extends parallel to the long axis of the tool and from the distal edge of the third tool projection to a second location on the first sloped surface;
the second distance is greater than the plate projection thickness.

6. The bone fixation system of claim 4 wherein the post includes a hollow conduit that extends from a proximal end of the tool to a distal end of the tool.

7. The bone fixation system of claim 6, wherein the number of tool projections equals the number of plate reliefs.

8. The bone fixation system of claim 6, wherein:
a first circular circumference is included in a plane that is orthogonal to the long axis of the tool;
the first circular circumference contacts an outermost tip of the first tool projection and an outermost tip of the second tool projection;
the first circular circumference has a first maximum diameter;
a second circular circumference is included in a plane that is orthogonal to the long axis of the aperture;
the second circular circumference contacts an outermost tip of the first plate relief projection and an outermost tip of the second plate relief;
the second circular circumference has a second maximum diameter;
the second maximum diameter is greater than the first maximum diameter.

9. The bone fixation system of claim 8, wherein:
a third circular circumference is included in a plane that is orthogonal to the long axis of the aperture;
the third circular circumference contacts an innermost edge of the first plate relief and an innermost edge of the second plate relief;
the third circular circumference has a third maximum diameter;
the third maximum diameter is less than the first maximum diameter.

10. The bone fixation system of claim 2 wherein the first tool projection is proportioned to pass through the first plate relief when the tool is being fixed to the plate.

11. The bone fixation system of claim 2 wherein:
the plate includes no threads between the first and second openings;
the plate includes no resilient members between the first and second openings;
the first opening directly interfaces a first outer surface of the plate;
the second opening directly interfaces a second outer surface of the plate;
the first outer surface of the plate opposes the second outer surface of the plate.

12. The bone fixation system of claim 11 wherein:
the first opening has a first maximum diameter that is orthogonal to the long axis of the aperture;
the second opening has a second maximum diameter that is orthogonal to the long axis of the aperture;
the second maximum diameter is greater than the first maximum diameter.

13. The bone fixation system of claim 1, wherein: (a) no portion of the aperture is threaded; (b) measured orthogonal to the long axis of the aperture, the second opening is wider than the first opening, and (c) measured parallel to the long axis of the aperture, the plate reliefs are further from the first opening than the second opening.

14. The bone fixation system of claim 13 wherein:
the aperture includes a counterbore;
the counterbore includes the first surface, the first surface being defined by a plane;
the plane is orthogonal to the long axis of the aperture;
the counterbore includes a sidewall, the sidewall extending parallel to the long axis of the aperture.

15. The bone fixation system of claim 13 comprising the bone anchor, wherein:
the bone anchor: (a) includes a head and a body, the head being coupled to the body, (b) has a long axis, (c) the body has an outer diameter that is orthogonal to the long axis and the head has an outer diameter that is orthogonal to the long axis, and (a)(iv) the outer diameter of the head is greater than the outer diameter of the body;
the bone anchor and the plate reliefs are collectively configured such that threads of the bone anchor head deform the first surface adjacent at least one of the plate reliefs when the bone anchor mates with the plate;
the bone anchor and the plate reliefs are collectively configured to lock the bone anchor to the plate in response to the threads of the bone anchor head deforming the first surface.

* * * * *